United States Patent [19]

Civelli et al.

[11] Patent Number: 5,594,108
[45] Date of Patent: Jan. 14, 1997

[54] HUMAN DOPAMINE RECEPTOR AND ITS USES

[75] Inventors: Olivier Civelli, Portland, Oreg.; Hubert H. Van Tol, Toronto, Canada

[73] Assignee: State of Oregon, Acting by and Through the Oregon State Board of Higher Education on Behalf of the Oregon Health Sciences University, Portland, Oreg.

[21] Appl. No.: 333,977

[22] Filed: Nov. 3, 1994

Related U.S. Application Data

[62] Division of Ser. No. 626,618, Dec. 7, 1990, Pat. No. 5,422,268.

[51] Int. Cl.[6] .................................................. C07K 14/705
[52] U.S. Cl. ............................................ 530/350; 530/395
[58] Field of Search ................................. 530/350, 345; 435/69.1; 536/23.5

*Primary Examiner*—John Ulm
*Attorney, Agent, or Firm*—Banner & Allegretti, Ltd.

[57] ABSTRACT

The present invention is directed toward the isolation, characterization and pharmacological use of the human $D_4$ dopamine receptor. The nucleotide sequence of the gene corresponding to this receptor is provided by the invention. The invention also includes a recombinant eukaryotic expression vector capable of expressing the human $D_4$ dopamine receptor in cultures of transformed eukaryotic cells and such cultures of transformed eukaryotic cells which synthesize the human $D_4$ dopamine receptor.

1 Claim, 13 Drawing Sheets

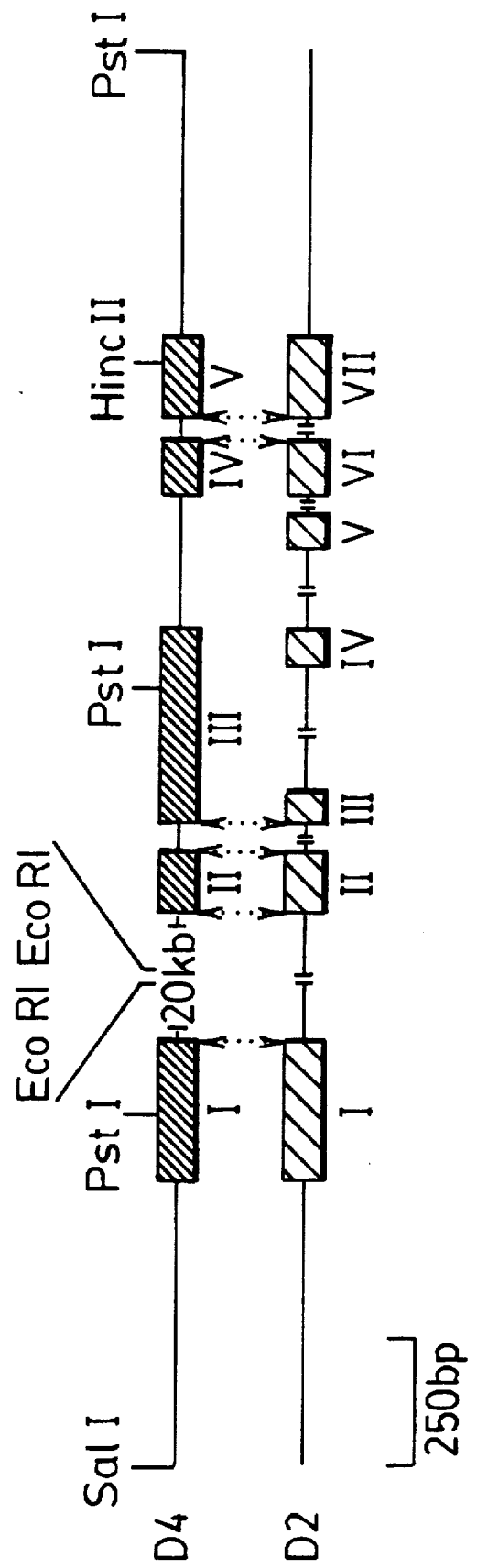

Figure 2A

```
5'-CGGGGGCGGGACCAGGGTCCGGCCGGGGCGTGCCCCC
GGGGAGGGACTCCCCGGCTTGCCCCCGGCGTTGTCCGCGGTG
                                +1
CTCAGCGCCCGCCCGGGCGCGCC ATG GGG AAC CGC AGC
                         MET GLY ASN ARG SER
                                              48
ACC GCG GAC GCG GAC GGG CTG CTG GCT GGG CGC
THR ALA ASP ALA ASP GLY LEU LEU ALA GLY ARG
                                    ▲
GGG CGG GCC GCG GGG GCA TCT GCG GGG GCA TCT
GLY PRO ALA ALA GLY ALA SER ALA GLY ALA SER
                                              114
GCG GGG CTG GCT GGG CAG GGC GCG GCG GCG CTG
ALA GLY LEU ALA GLY GLN GLY ALA ALA ALA LEU

GTG GGG GGC GTG CTG CTC ATC GGC GCG GTG CTC
VAL GLY GLY VAL LEU LEU ILE GLY ALA VAL LEU
                                              180
GCG GGG AAC TCG CTC GTG TGC GTG AGC GTG GCC
ALA GLY ASN SER LEU VAL CYS VAL SER VAL ALA

ACC GAG CGC GCC CTG CAG ACG CCC ACC AAC TCC
THR GLU ARG ALA LEU GLN THR PRO THR ASN SER
                                              246
TTC ATC GTG AGC CTG GCG GCC GCC GAC CTC CTC
PHE ILE VAL SER LEU ALA ALA ALA ASP LEU LEU

CTC GCT CTC CTG GTG CTG CCG CTC TTC GTC TAC
LEU ALA LEU LEU VAL LEU PRO LEU PHE VAL TYR

TCC GAG GTGAGCCGCGTCCGGCCGCA................
SER GLU

...CCTGTGGTGTCGCCGCGCAG GTC CAG GGT GGC GCG
                        VAL GLN GLY GLY ALA
                                              333
TGG CTG CTG AGC CCC CGC CTG TGC GAC GCC CTC
TRP LEU LEU SER PRO ARG LEU CYS ASP ALA LEU
```

Figure 2B

```
ATG GCC ATG GAC GTC ATG CTG TGC ACC GCC TCC
MET ALA MET ASP VAL MET LEU CYS THR ALA SER
                                            398
ATC TTC AAC CTG TGC GCC ATC AGC GTG GAC AG
ILE PHE ASN LEU CYS ALA ILE SER VAL ASP ARG

GTGCCGCCCTCCCCGCCCGCGCCCCGGCGCCCCGCGCCCC

GCCCGCCGCCCTCACCGCGGCCTGTGCGCTGTCCGGCGCCCCC

TCGGCGCTCCCCGCAG  G TTC GTG GCC GTG GCC GTG
                    PHE VAL ALA VAL ALA VAL
                                            450
CCG CTG CGC TAC AAC CGG CAG GGT GGG AGC CGC
PRO LEU ARG TYR ASN ARG GLN GLY GLY SER ARG

CGG CAG CTG CTG CTC ARC GGC GCC ACG TGG CTG
ARG GLN LEU LEU LEU ILE GLY ALA THR TRP LEU
                                         □ 516
CTG TCC GCG GCG GTG GCG GCG CCC GTA CTG TGC
LEU SER ALA ALA VAL ALA ALA PRO VAL LEU CYS

GGC CTC AAC GAC GTG CGC GGC CGC GAC CCC GCC
GLY LEU ASN ASP VAL ARG GLY ARG ASP PRO ALA
                                            582
GTG TGC CGC CTG GAG GAC CGC GAC TAC GTG GTC
VAL CYS ARG LEU GLU ASP ARG ASP TYR VAL VAL

TAC TCG TCC GTG TGC TCC TTC TTC CTA CCC TGC
TYR SER SER VAL CYS SER PHE PHE LEU PRO CYS
                                            648
CCG CTC ATG CTG CTG CTG TAC TGG GCC ACG TTC
PRO LEU MET LEU LEU LEU TYR TRP ALA THR PHE

CGC GGC CTG CAG CGC TGG GAG GTG GCA CGT CGC
ARG GLY LEU GLN ARG TRP GLU VAL ALA ARG ARG
                                            714
GCC AAG CTG CAC GGC CGC GCG CCC CGC CGA CCC
ALA LYS LEU HIS GLY ARG ALA PRO ARG ARG PRO
```

Figure 2C

```
AGC GGC CCT GGC CCG CCT TCC CCC ACG CCA CCC
SER GLY PRO GLY PRO PRO SER PRO THR PRO PRO
                                          780
GCG CCC CGC CTC CCC CAG GAC CCC TGC GGC CCC
ALA PRO ARG LEU PRO GLN ASP PRO CYS GLY PRO
GAC TGT GCG CCC CCC GCG CCC GGC CT TCCCCGGG
ASP CYS ALA PRO PRO ALA PRO GLY LEU
GTCCTGCGGCC......CCTGTGCGCCCCCGCGCCCGGCCT
CCCCAGGACCCCTGCGGCCCCGACTGTGCGCCCCCGCGCCC
                                          834
GGCCT C CCC CCG GAC CCC TGC GGC TCC AAC TGT
      PRO PRO ASP PRO CYS GLY SER ASN CYS
GCT CCC CCC GAC GCC GTC AGA GCC GCC GCG CTC
ALA PRO PRO ASP ALA VAL ARG ALA ALA ALA LEU
                                          900
CCA CCC CAG ACT CCA CCG CAG ACC CGC AGG AGG
PRO PRO GLN THR PRO PRO GLN THR ARG ARG ARG
CGG CGT GCC AAG ATC ACC GGC CGG GAG CGC AAG
ARG ARG ALA LYS ILE THR GLY ARG GLU ARG LYS
GCC ATG AGG GTC CTG CCG GTG GTG GTC G GTGG
ALA MET ARG VAL LEU PRO VAL VAL VAL
GTTCCTGTCCTGAGGGGCGGGGAGGAGAGGAGGGGGGGAGTAC
GAGGCCGGCTGGGCGGGGGGCGCTAACGCGGCTCTCGGCGCCC
CCAG GG GCC TTC CTG CTG TGC TGG ACG CCC TTC
     GLY ALA PHE LEU LEU CYS TRP THR PRO PHE
                                          1023
TTC GTG GTG CAC ATC ACG CAG GCG CTG TGT CCT
PHE VAL VAL HIS ILE THR GLN ALA LEU CYS PRO
```

Figure 2D

```
GCC TGC TCC GTG CCC CCG CGG CTG GTC AGC GCC
ALA CYS SER VAL PRO PRO ARG LEU VAL SER ALA
                                          1089
GTC ACC TGG CTG GGC TAC GTC AAC AGC GCC CTC
VAL THR TRP LEU GLY TYR VAL ASN SER ALA LEU

ACC CCC GTC ATC TAC ACT GTC TTC AAC GCC GAG
ASN PRO VAL ILE TYR THR VAL PHE ASN ALA GLU
                                          1155
TTC CGC AAC GTC TTC CGC AAG GCC CTG CGT GCC
PHE ARG ASN VAL PHE ARG LYS ALA LEU ARG ALA
    1164
TGC TGC TGA GCCGGGCACCCCCGGACGCCCCCCGGCCTG
CYS CYS STOP

ATGGCCAGGCCTCAGGGACCAAGGAGATGGGGAGGGCGCTTTT

GTACGTTAATTAAACAAATTCCTTCCCAAACTCAGCTGTGAAG
                                AAAAAAAAAAAAAAAAA
GCTCCTGGG-3'
AA
```

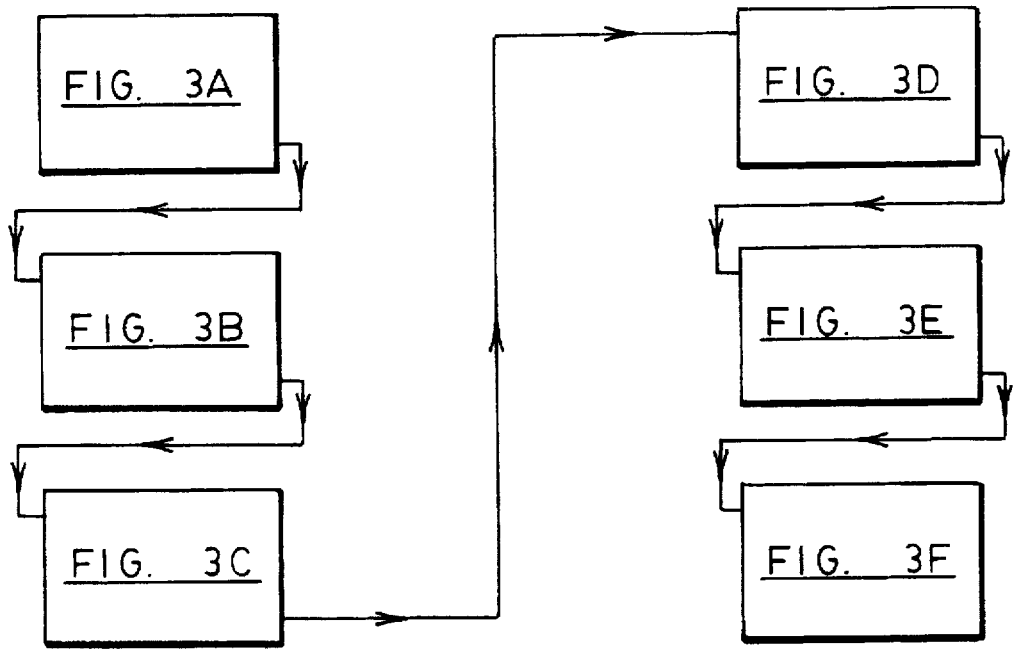

FIG. 3

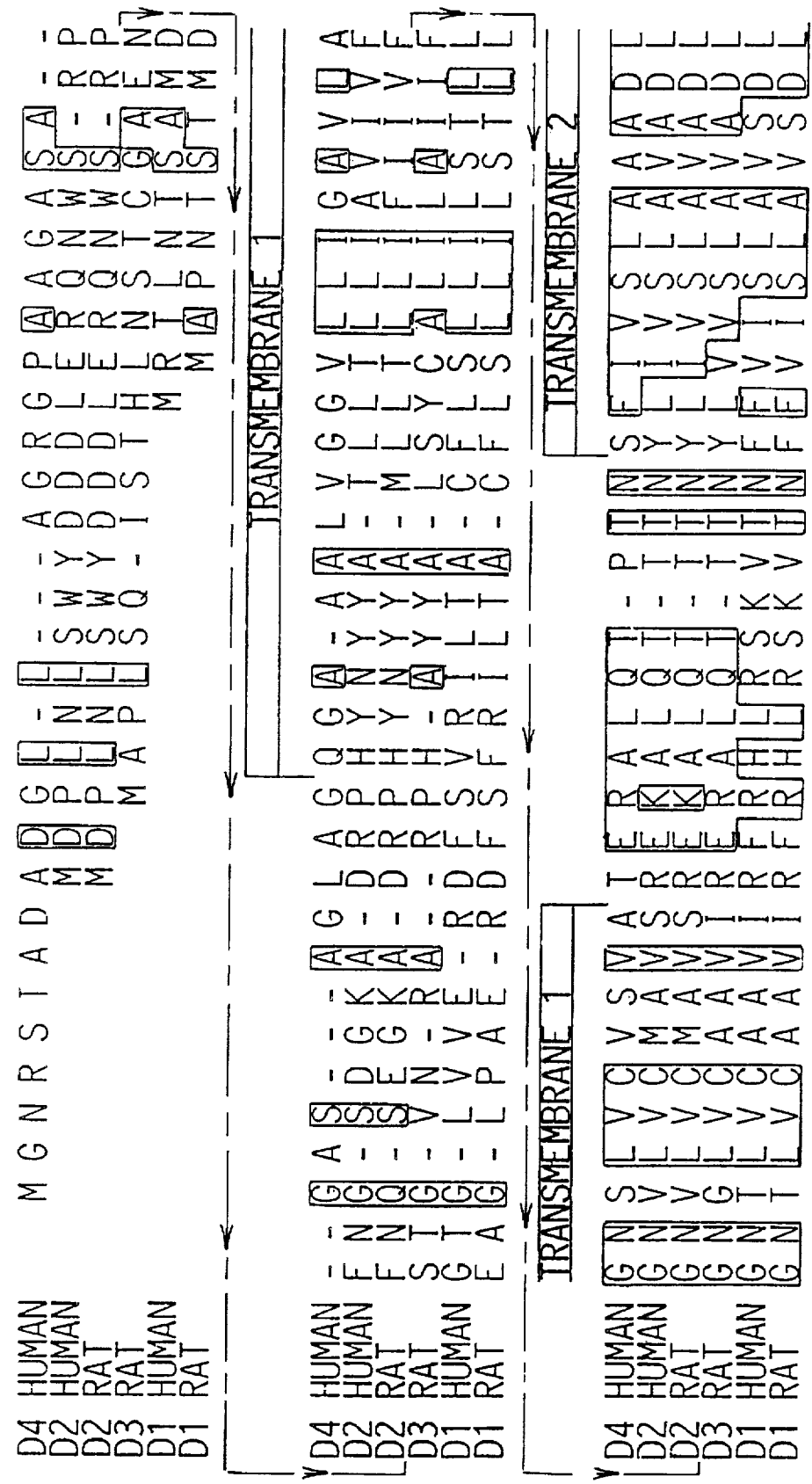

```
D1 HUMAN  P A T N N A I E T V S I N N N G A A M F S S H H E P R G S I S K
D1 RAT    P T T N N A I E T V S I N N N G A V F S S H H E P R G S I S K

D1 HUMAN  E C N L V Y L I P H A V G S S E D L K K E E A A G I A R P L E K
D1 RAT    D C N L V Y L I P H A V G S S E D L K K E E A G G I A K P L E K

D1 HUMAN  L S P A L S V I L D Y D T D V S L E K I Q P I T Q N G Q H P T
D1 RAT    L S P A L S V I L D Y D T D V S L E K I Q P V T H S G Q H S T

D1 HUMAN  446
D1 RAT    446
```

HUMAN DOPAMINE RECEPTOR AND ITS USES

BACKGROUND OF THE INVENTION

This invention was made with government support under NIMH grant MH-45614 awarded by the National Institutes of Health. The government has certain rights in the invention.

This is a divisional of application Ser. No. 07/626,618 filed Dec. 7, 1990, now U.S. Pat. No. 5,422,268.

FIELD OF THE INVENTION

The invention relates to dopamine receptors from mammalian species and the genes corresponding to such receptors. In particular, it relates to the human dopamine receptor $D_4$. Specifically, the invention relates to the isolation, cloning and sequencing of the human $D_4$ receptor gene. The invention also relates to the construction of eukaryotic expression vectors capable of expression of the human $D_4$ dopamine receptor in cultures of transformed eukaryotic cells and the synthesis of the human $D_4$ dopamine receptor in such cultures. The invention relates to the use of such cultures of transformed eukaryotic cells producing the human $D_4$ dopamine receptor for the characterization of antipsychotic drugs.

INFORMATION DISCLOSURE

Dopamine is a neurotransmitter that participates in a variety of different functions mediated by the nervous system, including vision, movement, and behavior. See generally Cooper, J. et al., "The Biochemical Basis of Neuropharmacology," 161–195 (Oxford University Press, N.Y. 3d Ed. 1978). The diverse physiological actions of dopamine are in turn mediated by its interaction with two of the basic types of G protein-coupled receptors: $D_1$ and $D_2$, which respectively stimulate and inhibit the enzyme adenylyl cyclase. Kebabian, J. and Calne, D., Nature 277: 93–96 (1979). Alterations in the number or activity of these receptors may be a contributory factor in disease states such as Parkinson's disease (a movement disorder) and schizophrenia (a behavioral disorder).

A great deal of information has accumulated on the biochemistry of the $D_1$ and $D_2$ dopamine receptors, and methods have been developed to solubilize and purify these receptor proteins. See Senogles, S. et al., Biochemistry 25: 749–753 (1986); Sengoles, S. et al., J. Biol. Chem. 263: 18996–19002 (1988); Gingrich, J. et al., Biochemistry 27: 3907–3912 (1988); Gingrich, J. et al. (in press). The $D_1$ dopamine receptor in several tissues appears to be a glycosylated membrane protein of about 72 kDa. Amlaiky, N. et al., Mol. Pharmacol. 31: 129–134 (1987); Ninik, H. et al., Biochemistry 27: 7594–7599 (1988). The $D_2$ receptor has been suggested to have a higher molecular weight of about 90–150 kDa. Amlaiky, N. and Caron, M., J. Biol. Chem. 260: 1983–1986 (1985); Amlaiky, N. and Caron, M., J. Neurochem. 47: 196–204 (1986); Jarvie, J. et al., Mol. Pharmacol. 34: 91–97 (1988). Much less is known about a recently discovered additional dopamine receptor, termed $D_3$. Sokoloff, P. et al., Nature 347: 146–151 (1990). Dopamine receptors are primary targets in the clinical treatment of psychomotor disorders such as Parkinson's disease and affective disorders such as schizophrenia. Seeman, P. et al., Neuropsychopharm. 1: 5–15 (1987); Seeman, P., Synapse 1: 152–333 (1987). The three different dopamine receptors ($D_1$, $D_2$, $D_3$) have been cloned as a result of nucleotide sequence homology which exists between these receptor genes. Bunzow, J. R. et al., Nature 336: 783–787 (1988); Grandy, D. K. et al., Proc. Natl. Acad. Sci. U.S.A. 86: 9762–9766 (1989); Dal Toso, R. et al., EMBO J. 8: 4025–4034 (1989); Zhou, Q-Y. et al., Nature 346: 76–80 (1990); Sunahara, R. K. et al., Nature 346: 80–83 (1990); Sokoloff, P. et al., Nature 347: 146–151 (1990).

The antipsychotic clozapine is useful for socially withdrawn and treatment-resistant schizophrenics [Kane, J. et al., Nature 347: 146–151 (1990)], but unlike other antipsychotic drugs, clozapine does not cause tardive dyskinesia [Casey, D. E., Psychopharmacology 99: 547–553 (1989)]. Clozapine, however, has dissociation constants at $D_2$ and $D_3$ which are 3 to 30-fold higher than the therapeutic free concentration of clozapine in plasma water [Ackenheil, M. et al., Arzneim-Forsch 26: 1156–1158 (1976); Sandoz Canada, Inc., Clozaril: Summary of preclinical and clinical data (1990)]. This suggests the existence of dopamine receptors more sensitive to the antipsychotic clozapine.

We have cloned and sequenced such a human dopamine receptor which we term $D_4$. The dopamine $D_4$ receptor gene has high homology to the human dopamine $D_2$ and $D_3$ receptor genes. The pharmacological profile of this receptor resembles that of the $D_2$ and $D_3$ receptors but it has an affinity for clozapine which is tenfold higher. The present inventors envision that the D4 dopamine receptor disclosed as this invention may prove useful in discovering new types of drugs for schizophrenia that like clozapine do not induce tardive dyskinesia and other motor side effects.

SUMMARY OF THE INVENTION

The present invention is directed toward the isolation, characterization and pharmacological use of the human $D_4$ dopamine receptor, the gene corresponding to this receptor, a recombinant eukaryotic expression vector capable of expressing the human $D_4$ dopamine receptor in cultures of transformed eukaryotic cells and such cultures of transformed eukaryotic cells that synthesize the human $D_4$ dopamine receptor.

It is an object of the invention to provide a nucleotide sequence encoding a mammalian dopamine receptor. Further, it is an object of the invention to provide a nucleotide sequence that encodes a mammalian dopamine receptor with novel and distinct pharmacological properties. It is specifically an object of the invention to provide a nucleotide sequence encoding a mammalian dopamine receptor having the particular drug dissociation properties of the human dopamine receptor $D_4$. In particular, the mammalian dopamine receptor encoded by the nucleotide sequence of the present invention has a high affinity for the drug clozapine. The human $D_4$ dopamine receptor embodied in the present invention shows a biochemical inhibition constant (termed $K_i$) of 1–40 nanomolar (nM), preferably 1–20 nM, most preferably 11 nM clozapine, as detected by the [$^3$H]spiperone binding assay disclosed herein. The human $D_4$ dopamine receptor embodied in the present invention displays the following pharmacological profile of inhibition of [$^3$H] spiperone binding in the [$^3$H]spiperone binding assay: spiperone>eticlopride>clozapine>(+)-butaclamol> raclopride>SCH23390. In a preferred embodiment of the invention, the nucleotide sequence encoding a dopamine receptor encodes the human dopamine receptor $D_4$.

The present invention includes a nucleotide sequence encoding a mammalian dopamine receptor derived from a cDNA molecule isolated from a cDNA library constructed with RNA from the human neuroblastoma cell line SK-N-MC. In this embodiment of the invention, the nucleotide sequence includes 780 nucleotides of the human $D_4$ dopamine receptor gene comprising transmembrane domains V, VI and VII and 126 nucleotides of 3' untranslated sequence (SEQ ID NOS.: 8, 12 & 15).

The invention also includes a nucleotide sequence derived from human genomic DNA (SEQ ID NOS.: 1, 3–5, 7, 8, 10–12, 14 & 15). In this embodiment of the invention, the nucleotide sequence includes 5 kilobases (kb) of human genomic DNA encoding the dopamine receptor $D_4$. This embodiment includes the sequences present in the cDNA embodiment, an additional 516 nucleotides of coding sequence comprising transmembrane domains I, II, III, and IV, and 590 nucleotides of 5' untranslated sequence. This embodiment of the invention also contains the sequences of four intervening sequences that interrupt the coding sequence of the human $D_4$ dopamine receptor gene.

The invention includes a nucleotide sequence of a human $D_4$ receptor molecule, and includes allelic variations of this nucleotide sequence and the corresponding $D_4$ receptor molecule, either naturally occurring or the product of in vitro chemical or genetic modification, having essentially the same nucleotide sequence as the nucleotide sequence of the human $D_4$ receptor disclosed herein, wherein the resulting human $D_4$ receptor molecule has substantially the same drug dissociation properties of the human $D_4$ receptor molecule corresponding to the nucleotide sequence described herein.

The invention also includes a predicted amino acid sequence for the human $D_4$ dopamine receptor deduced from the nucleotide sequence comprising the complete coding sequence of the $D_4$ dopamine receptor gene (SEQ ID NOS.: 2, 6, 9, 13 & 16 and SEQ ID NO. 17).

This invention provides both nucleotide and amino acid probes derived from these sequences. The invention includes probes isolated from either the cDNA or genomic DNA clones, as well as probes made synthetically with the sequence information derived therefrom. The invention specifically includes but is not limited to oligonucleotide, nick-translated, random primed, or in vitro amplified probes made using the cDNA or genomic clone embodying the invention, and oligonucleotide and other synthetic probes synthesized chemically using the nucleotide sequence information of the cDNA or genomic clone embodiments of the invention.

It is a further object of this invention to provide sequences of the human $D_4$ dopamine receptor for use as a probe to determine the pattern, amount and extent of expression of this receptor in various tissues of mammals, including humans. It is also an object of the present invention to provide probes derived from the sequences of the human $D_4$ dopamine receptor to be used for the detection and diagnosis of genetic diseases. It is an object of this invention to provide probes derived from the sequences of the human $D_4$ dopamine receptor to be used for the detection of novel related receptor genes.

The present invention also includes synthetic peptides made using the nucleotide sequence information comprising the cDNA or genomic clone embodiments of the invention. The invention includes either naturally occurring or synthetic peptides which may be used as antigens for the production of $D_4$ dopamine receptor-specific antibodies, or used for competitors of the $D_4$ receptor molecule for drug binding, or to be used for the production of inhibitors of the binding of dopamine or dopamine analogs of the $D_4$ dopamine receptor molecule.

In addition, this invention includes a cloning vector comprising the human $D_4$ dopamine receptor and sequences that mediate the replication and selected growth of microorganisms that carry this vector.

The present invention provides a recombinant expression vector comprising the nucleotide sequence of the human $D_4$ dopamine receptor and sequences sufficient to direct the synthesis of human $D_4$ dopamine receptor in cultures of transformed eukaryotic cells. In a preferred embodiment, the recombinant expression vector is comprised of plasmid sequences derived from the plasmid pCD-PS and a hybrid human $D_4$ dopamine gene. This hybrid human $D_4$ dopamine gene is comprised of the entirety of the genomic sequences from a particular $D_4$ dopamine genomic clone described herein, up to a PstI site located in exon III, followed by the remainder of the coding and 3' untranslated sequences found in a particular human cDNA sequence derived from a human neuroblastoma cell line. This invention includes a recombinant expression vector comprising essentially the nucleotide sequences of genomic and cDNA clones of the human $D_4$ dopamine receptor in an embodiment that provides for their expression in cultures of transformed eukaryotic cells.

It is also an object of this invention to provide cultures of transformed eukayotic cells that have been transformed with such a recombinant expression vector and that synthesize human $D_4$ dopamine receptor protein. In a preferred embodiment, the invention provides monkey COS cells that synthesize human $D_4$ dopamine receptor protein.

The present invention also includes protein preparations of the human $D_4$ dopamine receptor, and preparations of membranes containing the human $D_4$ dopamine receptor, derived from cultures of transformed eukaryotic cells. In a preferred embodiment, cell membranes containing human $D_4$ dopamine receptor protein is isolated from culture of COS-7 cells transformed with a recombinant expression vector that directs the synthesis of human $D_4$ dopamine receptor.

It also an object of this invention to provide the human $D_4$ dopamine receptor for use in the in vitro screening of novel antipsychotic compounds. In a preferred embodiment, membrane preparations containing the human $D_4$ dopamine receptor, derived from cultures of transformed eukaryotic cells, are used to determine the drug dissociation properties of antipsychotic compounds in vitro. These properties are then used to characterize novel antipsychotic compounds by comparison to the binding properties of known antipsychotic compounds.

The present invention will also be useful for the in vivo detection of dopamine and a dopamine analog, known or unknown, either naturally occurring or as the embodiments of antipsychotic or other drugs.

It is an object of the present invention to provide a method for the quantitative detection of dopamine and a dopamine analog, either naturally occurring or as the embodiments of antipsychotic or other drugs. It is an additional object of the invention to provide a method to detect dopamine or a dopamine analog in blood, saliva, semen, cerebrospinal fluid, plasma, lymph, or any other bodily fluid.

DESCRIPTION OF THE DRAWINGS

FIG. 1. The structure of a genomic clone comprising the human $D_4$ dopamine receptor gene.

Restriction map of the genomic human dopamine $D_4$ receptor clone and alignment with the genomic intron/exon organization of the human dopamine $D_2$ receptor. Relevant restriction endonuclease sites in the $D_4$ receptor are indicated. The SalI site if part of the cloning site in EMBL3. The proposed coding regions are boxed and numbered in Roman numerals. Perfect matches of proposed intron/exon junction sites are indicated by connecting stippled bars between the receptor clones.

FIGS. 2A through 2D. The nucleotide sequence of genomic and cDNA clones of human $D_4$ dopamine receptor gene (SEQ ID NOS.: 1, 3–5, 7, 8, 10–12, 14 & 15).

Nucleotide and deduced amino acid sequence of the human dopamine receptor gene and cDNA. The putative coding sequence is in capitals (non-coding sequence is in italics) and deduced amino acid sequence is shown above the nucleotide sequence. Numbering of the putative coding sequence begins with the first methionine of the open reading frame. The sequence corresponding to the cDNA clone is hatched.

Figure 3B:
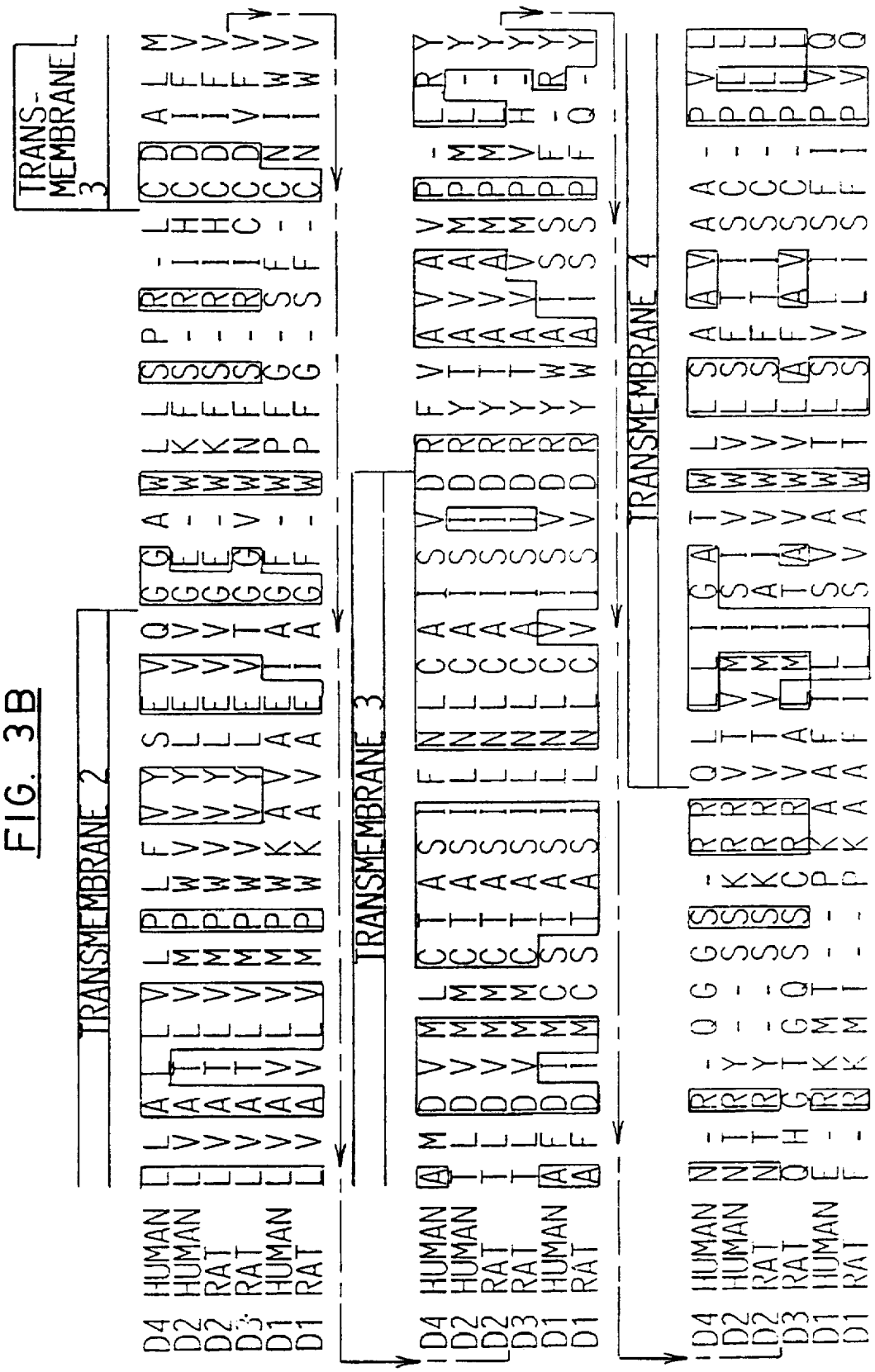
Figure 3C:
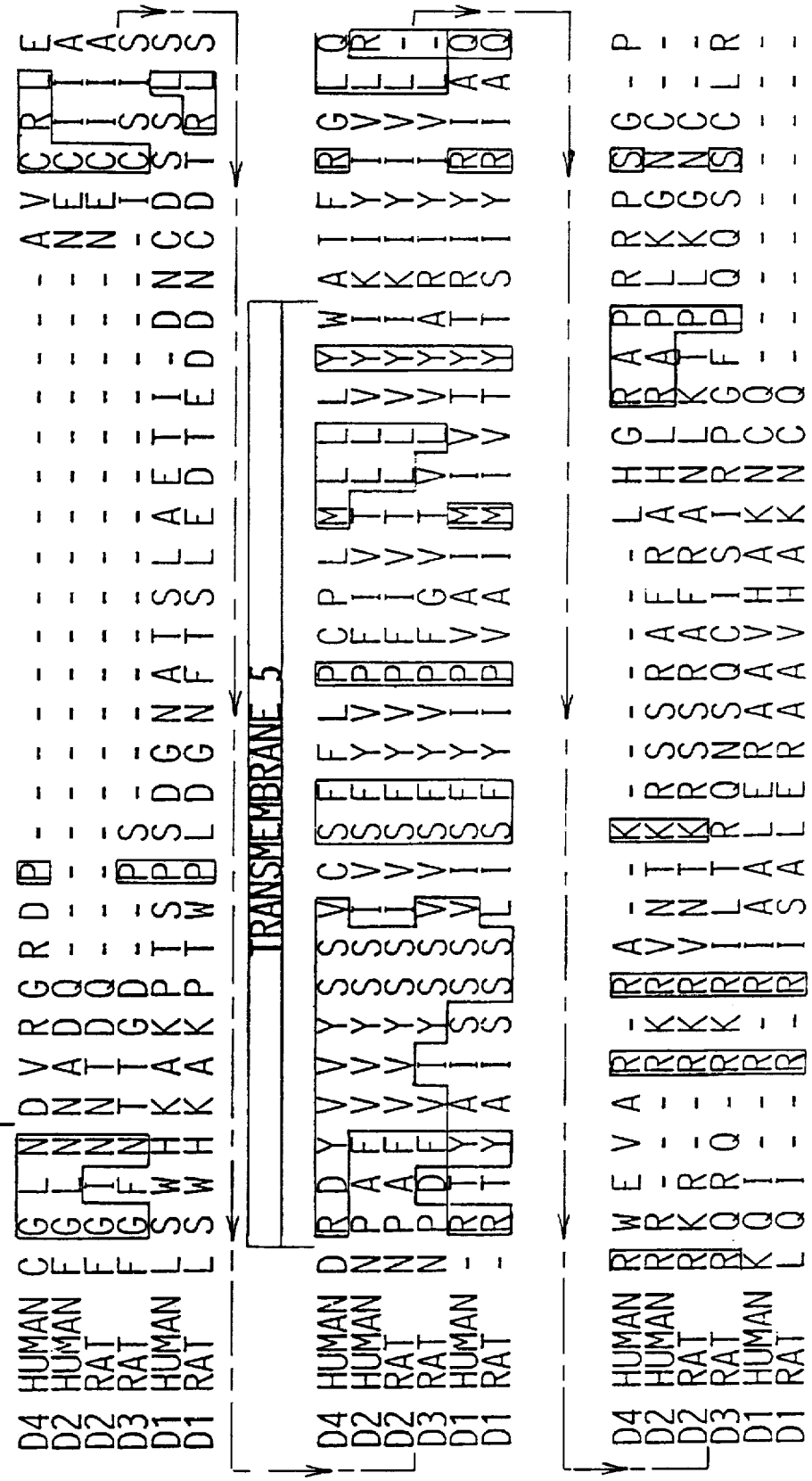
Figure 3D:
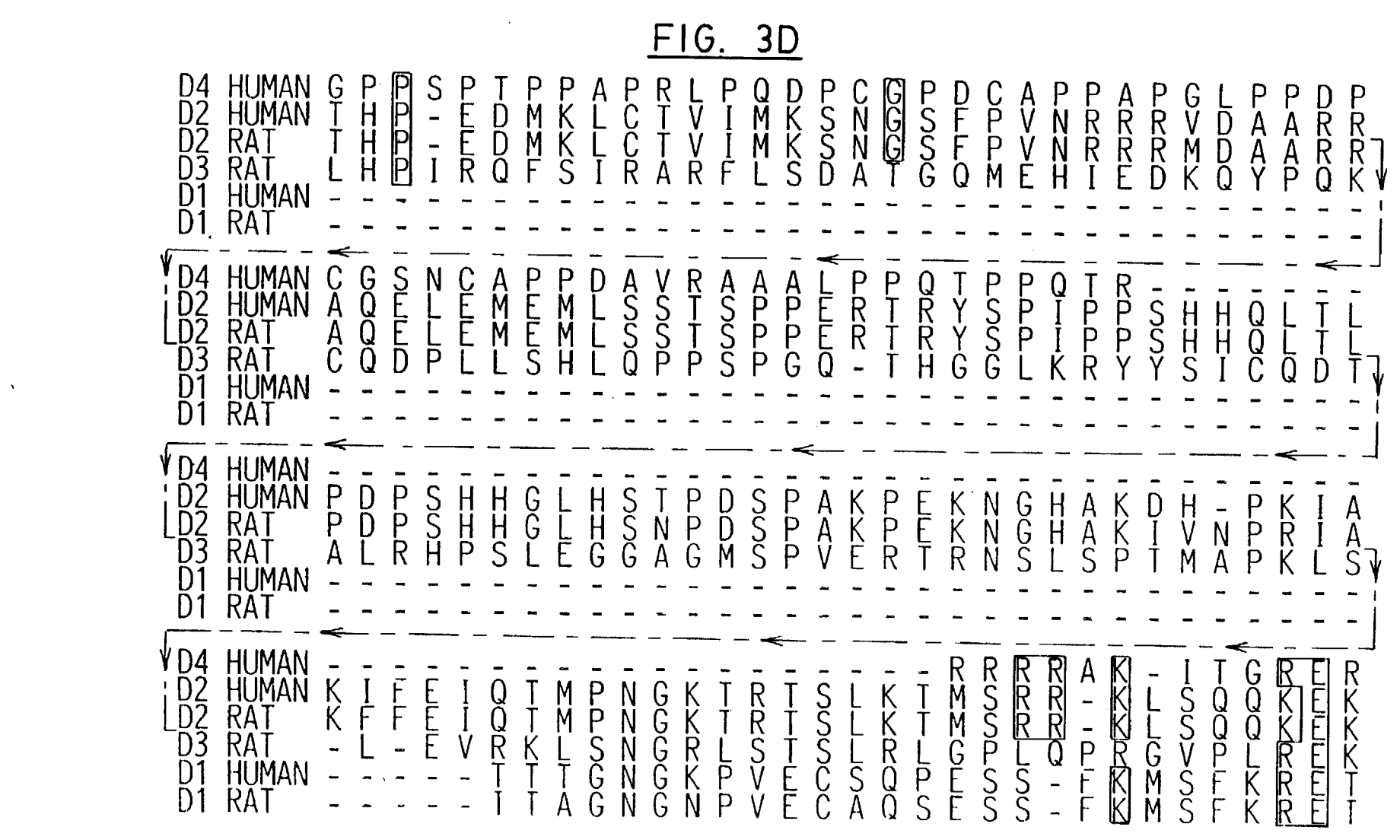
Figure 3E:
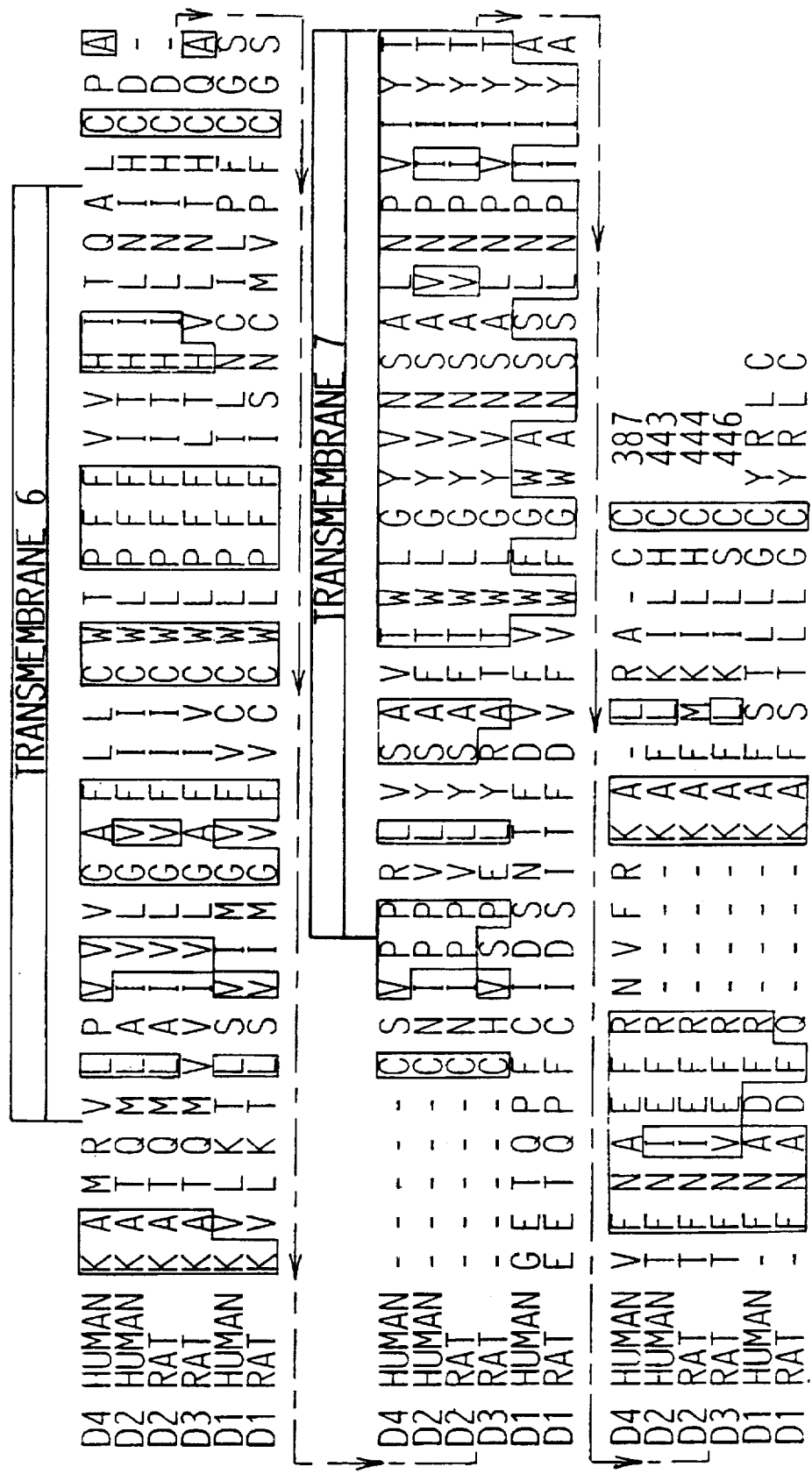

FIG. 3, which is composed of FIGS. 3A through 3F. Amino acid sequence alignment of mammalian dopamine receptors Alignment of the putative amino acid sequence of the human $D_4$ receptor (SEQ ID NO.: 17) with the human (SEQ ID NO.: 19) and rat (SEQ ID NO. 18) $D_2$, rat $D_3$ (SEQ ID NO.: 20) and human (SEQ ID NO: 21) and rat (SEQ ID NO: 22) $D_1$ receptors. Amino acids conserved within the group of dopamine receptors are shaded. The putative transmembrane domains are overlined and labeled by Roman numerals.

Figure 4B:
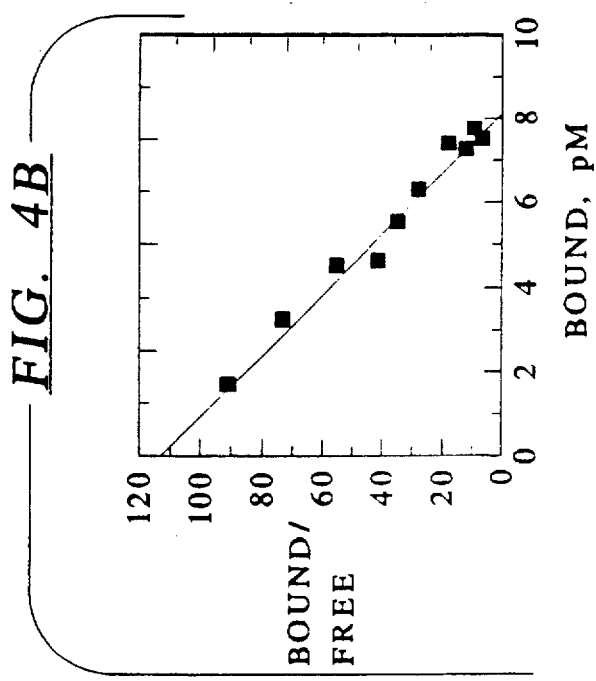
Figure 4A:
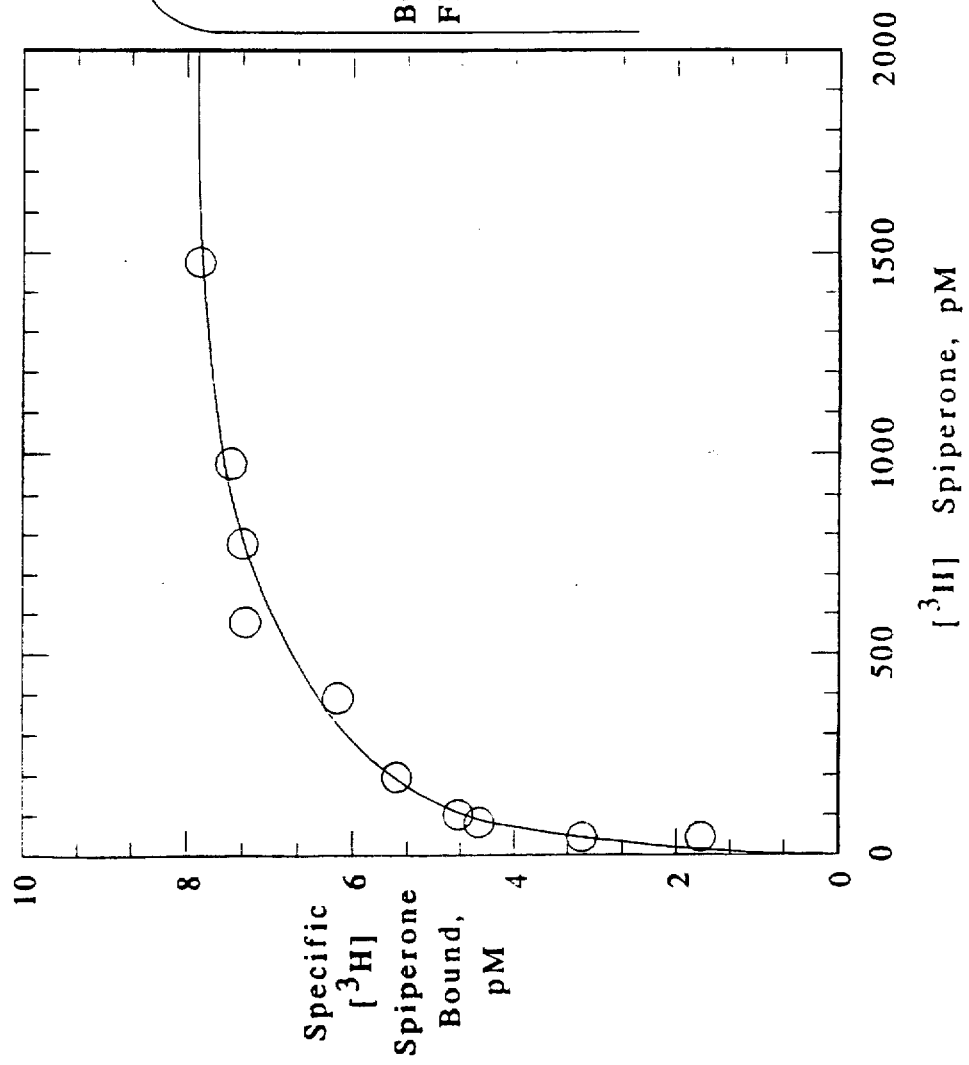

FIG. 4. Binding of [$^3$H]spiperone to transfected COS-7 cell membranes.

Saturation isotherms of the specific binding of [$^3$H]spiperone to membranes from COS-7 cells expressing the cloned human dopamine $D_4$ receptor. The results shown are representative of two independent experiments each conducted in duplicate. Inset, Scatchard plot of the same data. Estimated $B_{max}$ (approximately 260 fmol/mg protein) and $K_i$ (70 pM) values were obtained by LIGAND computer program.

Figure 5:
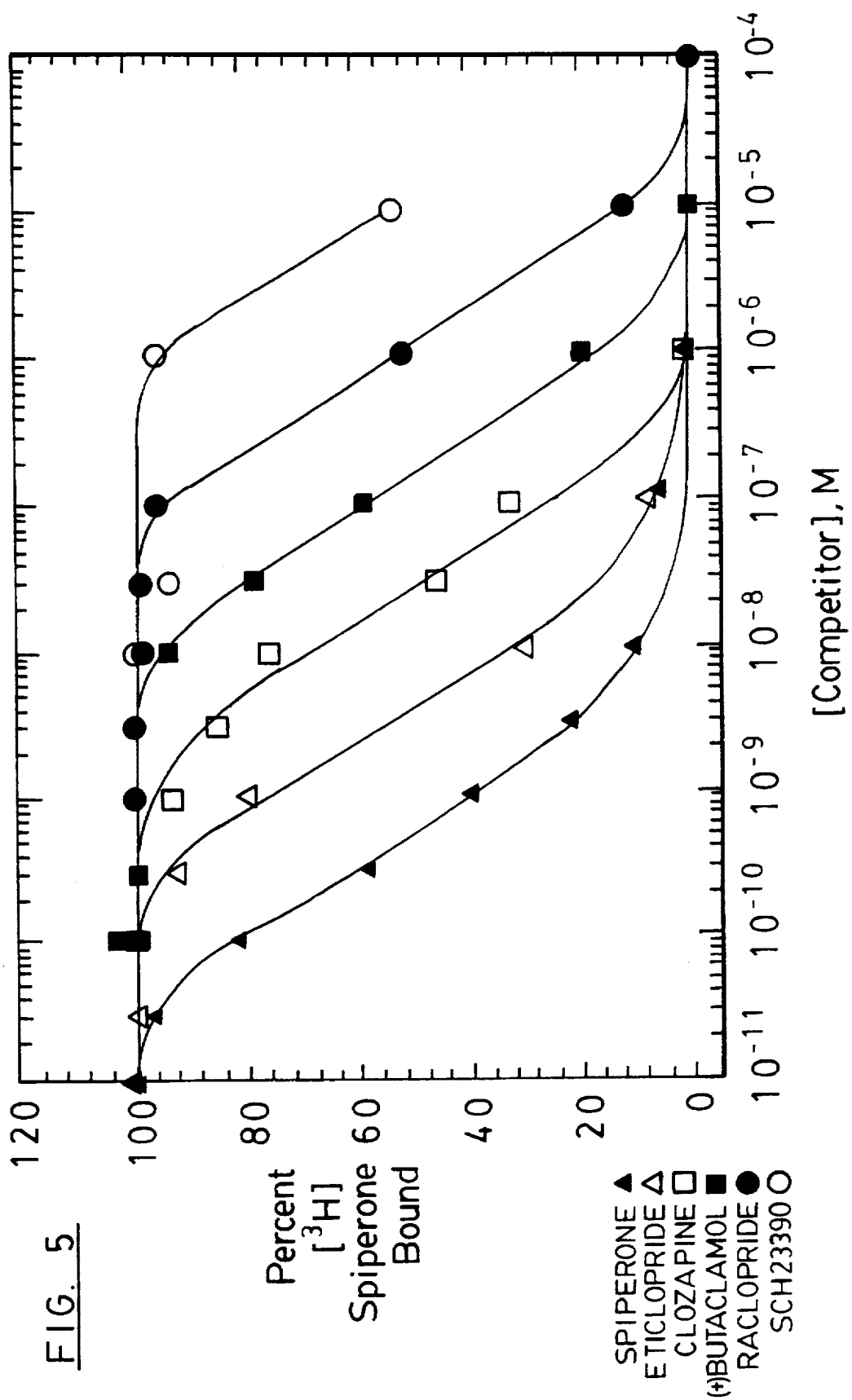

FIG. 5. Pharmacological specificity of [$^3$H]spiperone binding to transfected COS-7 cells.

Representative curves are shown for the concentration dependent inhibition of [$^3$H]spiperone binding by various dopaminergic agonist and antagonists. Data were analyzed by LIGAND and the results shown are the means of duplicate determinations. Estimated $K_i$ values are listed in Table I along with the $K_i$ values obtained on the human $D_2$ receptor expressed in $GH_4ZR7$ cells.

DETAILED DESCRIPTION OF THE PREFERRED EMBODIMENTS

The term "$D_4$-dopamine receptor" as used herein refers to proteins substantially homologous to, and having substantially the same biological activity as, the protein coded for by the nucleotide sequence depicted in FIGS. 2A through 2D (i.e., proteins which display high affinity binding to clozapine). This definition is intended to encompass natural allelic variations in the $D_4$-dopamine receptor sequence. Cloned genes of the present invention may code for $D_4$-dopamine receptors of any species of origin, including, mouse, rat, rabbit, cat, and human, but preferably code for receptors of mammalian, most preferably human, origin.

Nucleotide bases are abbreviated herein as follows:

| | |
|---|---|
| A = Adenine | G = Guanine |
| C = Cytosine | T = Thymine |

Amino acid residues are abbreviated herein to either three letters or a single letter as follows:

| | |
|---|---|
| Ala;A = Alanine | Leu;L = Leucine |
| Arg;R = Arginine | Lys;K = Lysine |
| Asn;N = Asparagine | Met;M = Methionine |
| Asp;D = Aspartic acid | Phe;F = Phenylalanine |
| Cys;C = Cysteine | Pro;P = Proline |
| Gln;Q = Glutamine | Ser;S = Serine |
| Glu;E = Glutamic acid | Thr;T = Threonine |
| Gly;G = Glycine | Trp;W = Tryptophan |
| His;H = Histidine | Tyr;Y = Tyrosine |
| Ile;I = Isoleucine | Val;V = Valine |

The production of proteins such as the $D_4$-dopamine receptor from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the $D_4$-dopamine receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the $D_4$-dopamine receptor gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, $D_4$-dopamine receptor gene sequences may be obtained by use of the polymerase chain reaction (PCR) procedure, with the PCR oligonucleotide primers being produced from the $D_4$-dopamine receptor gene sequence provided herein. See U.S. Pat. No. 4,683,195 to Mullis et al. and U.S. Pat. No. 4,683,202 to Mullis.

The $D_4$-dopamine receptor may be synthesized in host cells transformed with vectors containing DNA encoding the $D_4$-dopamine receptor. A vector is a replicable DNA construct. Vectors are used herein either to amplify DNA encoding the $D_4$-dopamine receptor and/or to express DNA which encodes the $D_4$-dopamine receptor. An expression vector is a replicable DNA construct in which a DNA sequence encoding the $D_4$ receptor is operably linked to suitable control sequences capable of effecting the expression of the $D_4$ receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself.

Suitable vectors will contain replicon and control sequences which are derived from species compatible with the intended expression host. Transformed host cells are cells which have been transformed or transfected with the $D_4$ receptor vectors constructed using recombinant DNA techniques. Transformed host cells ordinarily express the $D_4$ receptor, but host cells transformed for purposes of cloning or amplifying the $D_4$ receptor DNA need not express the $D_4$ receptor. When expressed, the $D_4$ receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Cultures of cells derived from multicellular organisms are a desirable host for recombinant $D_4$-dopamine receptor synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture,* Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters of SV40 are useful because both are obtained easily from the virus as a fragment which also contains the SV40 viral origin of replication. See Fiers et al., *Nature* 273: 113 (1978). Further, the human genomic $D_4$ receptor promoter, control and/or signal sequences, may also be used, provided such control sequences are compatible with the host cell chosen.

An origin of replication may be provided either by construction of the vector to include an exogeneous origin, such as may be derived from SV40 or other viral source (e.g., Polyoma, Adenovirus, VSV, or MPV), or may be provided by the host cell chromosomal replication mechanism. If the vector is integrated into the host cell chromosome, the latter may be sufficient.

$D_4$-dopamine receptors made from cloned genes in accordance with the present invention may be used for screening compounds for $D_4$ dopamine receptor activity, or for determining the amount of a dopaminergic drug in a solution (e.g., blood plasma or serum). For example, host cells may be transformed with a vector of the present invention, $D_4$-dopamine receptors expressed in that host, the cells lysed, and the membranes from those cells used to screen compounds for $D_4$-dopamine receptor binding activity. Competitive binding assays in which such procedures may be carried out are well known, as illustrated by the Examples below. By selection of host cells which do not ordinarily express a dopamine receptor, pure preparations of membranes containing $D_4$ receptors can be obtained. Further, $D_4$-dopamine receptor agonist and antagonists can be identified by transforming host cells with vectors of the present invention. Membranes obtained from such cells can be used in binding studies wherein the drug dissociation activity is monitored. Such cells must contain $D_4$ protein in the plasma and other cell membranes. Procedures for carrying out assays such as these are also described in greater detail in the Examples which follow.

Cloned genes and vectors of the present invention are useful in molecular biology to transform cells which do not ordinarily express the $D_4$-dopamine receptor to thereafter express this receptor. Such cells are useful as intermediates for making cell membrane preparations useful for receptor binding assays, which are in turn useful for drug screening. Further, genes and vectors of the present invention are useful in gene therapy. For such purposes, retroviral vectors as described in U.S. Pat. No. 4,650,764 to Temin and Watanabe or U.S. Pat. No. 4,861,719 to Miller may be employed. Cloned genes of the present invention, or fragments thereof, may also be used in gene therapy carried out homologous recombination or site-directed mutagenesis. See generally Thomas, K. and Capecchi, M., *Cell* 51: 503–512 (1987); Bertling, W., *Bioscience Reports* 7: 107–112 (1987); Smithies, O. et al., *Nature* 317: 230–234 (1985).

Cloned genes of the present invention, and oligonucleotides derived therefrom, are useful for screening for restriction fragment length polymorphism (RFLP) associated with certain genetic disorders.

Oligonucleotides of the present invention are useful as diagnostic tools for probing $D_4$-receptor gene expression in nervous tissue. For example, tissue can be provided in situ with oligonucleotide probes carrying detectable groups by conventional autoradiography techniques, as explained in greater detail in the Examples below, to investigate native expression of this receptor or pathological conditions relating thereto. Further, chromosomes can be probed to investigate the presence or absence of a $D_4$-dopamine receptor gene, and potential pathological conditions related thereto, as also illustrated by the Examples below.

The Examples which follow are illustrative of specific embodiments of the invention, and various uses thereof. They are set forth for explanatory purposes only, and are not to be taken as limiting the invention.

EXAMPLE 1

Screening Tissue and Cell Line RNA for Dopamine-Like Receptor Expression

RNA was prepared from different rat tissues or cell lines using the guadinium thiocyanate/CsCl procedure described in Bunzow et al., *Nature* 336: 783–787 (1988). The tissues included heart, epididymis, testis, gut, pancreas, spleen, thymus, muscle, ventricle, atria, lung, adrenal, kidney, liver, pineal gland and pituitary. The cell lines screened included SK-N-MC, SK-N-SH, COS, AKR1, Ltk⁻, GH4C1, NG108-15, AtT20, 3T3, BSC40, C6, CV-1, Hela, IMR-32, N4TG1, NCB-20, PC-12, Rion m5f and WERI-Rb-1. 20 μg of RNA was analyzed by Northern blot hybridization with a radiolabeled BstYI-BglII DNA fragment of the rat $D_2$ receptor, which encodes the putative transmembrane domains VI and VII. The hybridization conditions used were 25% formamide, 1M NaCl, 1% SDS, 100 μg/ml denatured salmon sperm DNA, 0.2% polyvinylpirolidone, 0.2% Ficoll, and 0.05M Tris/HCl (pH 7.4); hybridization was performed overnight at 37° C. The blot was then washed at 55° C. in 2X standard saline-citrate (SSC) and 1% sodium dodecyl sulfate (SDS). Exposure was for two days at −70° C. using an intensifying screen. For comparison, the same blot was hybridized under high stringency conditions, which are the same conditions using 50% formamide and 42° C. for the hybridication and 0.2X SSC for the wash. Under high and low stringency only the adrenal gland showed a positive signal while under low stringency the SK-N-MC line also showed a signal.

EXAMPLE 2

Construction of a cDNA Phage Library using Neuroblastoma RNA

Double-stranded cDNA was synthesized using standard techniques [see Sambrook, J. et al., *Molecular Cloning: A Laboratory Manual*, 2d ed., Cold Spring Harbor Laboratory Press 1989] from poly(A)+mRNA isolated from the human neuroblastoma cell line SK-N-MC as described in Example 1. The cDNA was directionally cloned into the EcoRI and XhoI restriction endonuclease sites of the phage cloning vector lambda ZAPII (Stratagene, 11099 North Torrey Pines Road, La Jolla, Calif. 92037). The library was transferred to colony plaque screen filters (New England Nuclear, 549 Albany Street, Boston, Mass. 02118) and prehybridized overnight at 37° C. in 25% formamide, 0.2% polyvinylpyrolidone, 0.2% Ficoll, 0.05M Tris/HCl (pH 7.5), 1M NaCl, 0.1% pyrophosphate, 1% SDS and denatured salmon sperm DNA (100 μg/ml). Approximately 500,000 independent clones were screened under low-stringency conditions of hybridization. Hybridization was performed for 30 hrs with 1.6 kb BamHI-BglII and 300 bp BstYI-BglII fragments of a rat $D_2$ receptor clone, $^{32}$P-labeled using a random primed labeling system (Boehringer Mannheim Biochemicals, P.O. Box 50414, Indianapolis, Ind. 46250) at a specific activity of $10^6$ dpm/μg. Filters were washed at 55° C. in 2X SSC and 1% SDS. The clone $D_2$10S was isolated and sequenced using the Sanger dideoxy chain termination method catalyzed by Sequenase (U.S. Biochemical Corporation, P.O. Box 22400, Cleveland, Ohio 44122). The sequence of this clone is shown in FIGS. 2A through 2D (hatched area) (SEQ ID NO.: 8, 12 & 15).

EXAMPLE 3

Screening a Genomic DNA Phage Library with a Human Dopamine Receptor Probe

Clone $D_2$10S was $^{32}$P-labeled by random primed synthesis and used to screen a commercially available human genomic library cloned in the phage vector EMBL3 (Clonetech). Hybridization was performed as described in Example 2 using with 50% formamide. After hybridization the filters were washed at 65° C. in 0.1X SSC and 0.1% SDS. The clone $D_2$10G was isolated and analyzed by restriction endonuclease and Southern blot analysis. The map of this genomic clone is shown in FIG. 1, wherein the structure of the $D_4$ receptor gene is compared with the structure of the $D_2$ gene. 1.3 kg and 2.6 kb PstI-PstI fragments and an overlapping 2.0 kg SalI-EcoRI fragment of the $D_4$ receptor gene were subcloned into the plasmid pBluescript-SK (Stratagene). The subcloned fragments were characterized by sequence analysis as described above. This sequence is shown in (SEQ ID NOS.: 1, 3–5, 7, 8, 10–12, 14 & 15) FIGS. 2A through 2D.

EXAMPLE 4

DNA Sequence Analysis of the Human $D_4$ Dopamine Receptor

One of the cDNA clones detected by screening the SK-N-MC neuroblastoma library with a rat $D_2$ probe at low stringency ($D_2$10S) contained a 780 bp EcoRI-XhoI insert which hybridized to the rat probe. Sequence analysis of this insert showed the presence of an open reading frame with homology to the amino acid sequence of transmembrane domains V (45%), VI (46%) and VII (78%) of the $D_2$ receptor as shown in FIGS. 3A through 3F.

Screening of a human genomic EMBL3 library (Clontech) under high stringency conditions with the clone $D_2$10S resulted in the isolation of the genomic clone $D_2$10G. Southern blot and sequence analysis indicated that the clone contained a 5 kg SalI-PstI fragment which coded for the entire gene of $D_2$10S. Sequence analysis revealed, 590 bp downstream from the SalI site, a potential translation initiation codon (ATG) followed by an open reading frame that showed amino acid sequence homology with transmembrane domain I (36%) and II (63%) of the $D_2$ receptor. Almost immediately downstream from transmembrane domain II, homology to the $D_2$ receptor disappears, indicating the presence of an intron in the genomic DNA. This intron spanned approximately 2 kg, after which sequence homology to the $D_2$ receptor was re-established. Translation of the putative gene product showed homology to the transmembrane domains III (68%), IV (37%), V(46%) and VII (78%) of the $D_2$ receptor (see FIGS. 3A through 3F).

Potential splice junction donor and acceptor sites (Mount, *Nucl. Acids Res.* 10: 461–472, 1982) were found in the transmembrane domains II, III and VI, as shown in FIG. 1. These splice sites were at an identical position as in the $D_2$ and $D_3$ receptor gene [see Grandy, D. K. et al., *Proc. Natl. Acad. Sci. U.S.A.* 86: 9762–9766 (1989); Dal Toso, R. et al., *EBMO J.* 8: 4025–4034 (1989); Sokoloff, P. et al., *Nature* 347: 146–151 (1990)] and FIG. 1. The coding sequence downstream from transmembrane domain IV is identical to the sequence of clone $D_2$10S but is interrupted by an intron of about 300 bp between transmembrane domain V and VI and an additional intron of 92 bp in transmembrane VI (FIG. 1, hatched area). The precise location of the splice site for the intron between transmembrane V and VI cannot be determined due to the fact that a sequence of 52 bp present in the coding sequence is repeated exactly on either side of the intron (FIGS. 2A through 2D).

The deduced amino acid sequence from the genomic and cDNA nucleotide sequences indicated that this gene codes for a protein of 387 amino acids with an apparent molecular weight of 41 kD (SEQ ID NOS.: 2, 6, 9, 13 & 16 and SEQ ID NO.: 17). A hydrophobicity plot of the protein sequence suggests the existence of seven transmembrane domains. These regions correlate with the observed homologous regions in the human $D_2$ receptor and other receptors belonging to the family of G-protein coupled receptors [Bunzow, J. R. et al., *Nature* 336: 783–787 (1988); Sokoloff, P. et al., *Nature* 347: 146–151 (1990); Dohlman, H. G. et al., *Biochemistry* 26: 2657–2664 (1987) and FIGS. 2A through 2D]. Two amino acids downstream from the initiation methionine is a potential N-linked glycosylation site [Hubbard, S. & Ivatt, R. Annu. Rev. Biochem. 50: 555–583 (1981)]. The amino acid residues Asp (80) and Asp (115) in the $D_4$ receptor, which are conserved within the family catecholaminergic receptors, are postulated to act as centurions in catecholamine binding [Strader, C. D. et al., *J. Biol. Chem.* 263: 10267–10271 (1988)]. Also conserved within the family of catecholaminergic receptors are Ser (197) and Ser (700) which have been suggested to interact with the catechol hydroxyl groups [Kozak, M., *Nucleic Acids Res.* 12: 857–872 (1984)]. Several consensus sites for potential phosphorylation by protein kinase C and protein kinase A are noted in the 3rd cytoplasmic loop [Sibley, D. R. et al., *Cell* 48: 913–922 (1987); Bouvier, M. et al., *Nature* 333: 370–373 (1988)]. The Cys (187), which may serve as a substrate for palmitoylation, is conserved in most of the G-protein coupled receptors [O'Dowd, B. F. et al., *J. Biol. Chem.* 264: 7564–7569 (1989)]. The short carboxyl tail, which terminates similar to the $D_2$ and $D_3$ receptor at Cys (387) [Bunzow, J. R. et al., *Nature* 336: 783–787 (1988); Grandy, D. K. et al., *Proc. Natl. Acad. Sci. U.S.A.* 86: 9762–9766 (1989); Dal Toso, R. et al., *EMBO J.* 8: 4025–4034 (1989); Sokoloff, P. et al., *Nature* 347: 146–151 (1990)], and the relative large 3rd cytoplasmic loop, are features observed in most receptors which interact with an isoform of the G protein.

EXAMPLE 5

Construction of an Mammalian DNA Expression Vector using Dopamine Receptor cDNA The SalI-PstI gene fragment (FIG. 1, the PstI site found in exon III after transmembrane domain V) was ligated to the corresponding PstI-EcoRI cDNA fragment isolated from the SK-N-MC cDNA. This construct was then cloned into the vector pCD-PS [Bonner et al., *Neuron* 1: 403–410 (1988)]. This vector allows for the expression of the human $D_4$ receptor gene from the SV40 promoter. Large quantities of the pCD-PS-$D_4$ construct plasmid were prepared using standard techniques. This plasmid was transfected into COS-7 cells by the calcium phosphate precipitation technique [Gorman et al., *Science* 221: 551–553 (1983)]. Two days later membranes cells were harvested and analyzed as described in Example 6.

EXAMPLE 6

Analysis of Dopamine and Dopamine-Antagonist Binding of $D_4$ Dopamine Receptor Cells were harvested and homogenized using a teflon pestle in 50 mM Tris-HCl (pH 7.4 at 4° C.) buffer containing 5 mM EDTA, 1.5 mM $CaCl_2$, 5 mM $MgCl_2$, 5 mM KCl and 120 mM NaCl. Homogenates were centrifuged for 15 minutes at 39,000 g, and the resulting pellets resuspended in buffer at a concentration of 150–250 ug/ml. For saturation experiments, 0.25 ml aliquots of tissue homogenate were incubated in duplicate with increasing concentrations of [$^3$H]spiperone (70.3 Ci/mmol; 10–3000 pM final concentration) for 120 min at 22° C. in a total volume of 1 ml. The results of these experiments are shown in FIG. 4. For competition binding experiments, assays were initiated by the addition of 0.25 ml of membrane and incubated in duplicate with the concentrations of competing ligands indicated in FIG. 5 ($10^{-14}$ to $10^{-3}$M) and [$^3$H]spiperone (150–300 pM) for 120 min at 22° C. Assays were terminated by rapid filtration through a Titertek cell harvester and filters subsequently monitored to quantitate radioactive tritium.

For all experiments specific [$^3$H]spiperone binding was defined as that inhibited by 10 μM (+)sulpiride. Both saturation and competition binding data were analyzed by the non-linear least square curve-fitting program LIGAND run on a DIGITAL Micro-PP-11. The human $D_4$ dopamine receptor displays the following pharmacological profile of inhibition of [$^3$H]spiperone binding in this assay: spiperone>eticlopride>clozapine>(+)-butaclamol> raclopride>SCH23390 as shown in Table I.

TABLE I

| Dopamine Receptor Drug Dissociation Constants | | | |
|---|---|---|---|
| | $D_2$(long) $K_i$ | $D_4 K_i$ | $D_2 K_i$ / $D_4 K_i$ |
| Dopamine Antagonists | | | |
| Butaclamon-(+) | 0.9 H | 36 | 0.03 |
| Chlorpromazine | 2.8 R | 23 | 0.12 |
| Chlorpromazine | 1.5 H | 23 | 0.07 |
| Clozapine | ~130 T | 11 | 11.8 |
| Clozapine | 56 R | 11 | 5.1 |
| Clozapine | 158 H | 11 | 15.3 |
| Eticlopride | 0.09 T | 0.52 | 0.17 |
| Fluphenazine | 0.5 T | 42 | 0.01 |
| Haloperidol | 0.5 R | 4.5 | 0.11 |
| Haloperidol | 0.8 R | 4.5 | 0.18 |
| Haloperidol | 1 H | 4.5 | 0.22 |
| Ketanserin | 192 T | 147 | 1.31 |
| Octoclothepin-S | 1.5 T | 0.8 | 1.58 |
| Octoclothepin-R | 13.5 T | 1.9 | 7.11 |
| Pimozide | 2.4 R | 25 | 0.1 |
| Raclopride | 1.8 R | 253 | 0.01 |
| Raclopride | 1.6 H | 253 | 0.01 |
| *Raclopride | 3.2 H | 253 | 0.01 |
| Remoxipride | ~300 T | 2730 | 0.11 |
| SCH 23390 | 913 H | 1960 | 0.47 |
| Spiperone | 0.069 R | 0.06 | 1.15 |
| Spiperone | 0.053 H | 0.06 | 0.88 |
| *Spiperone | 0.05 H | 0.06 | 0.83 |
| *Spiperone | 0.09 H | 0.06 | 1.5 |
| Sulpiride-S | 9.2 R | 63 | 0.02 |
| Sulpiride-S | 4.8 R | 63 | 0.08 |
| Sulpiride-S | 46 H | 63 | 0.73 |
| Sulpiride-S | 15.9 H | 63 | 0.25 |
| Thioproperazine | 0.21 R | 53 | 0.004 |
| Thioridazine | 3.3 H | 12 | 0.28 |
| Trifluoperazine | 1.2 T | 2.2 | 0.55 |
| YM-09151-2 | 0.06 T | 0.11 | 0.55 |
| *YM-09151-2 | 0.09 H | 0.11 | 0.82 |
| Dopamine Agonists | | | |
| ADTN-(±) | 1.7 T | 33.7 | |
| Apomorphine | ~2 T | 3.3 | |
| Apomorphine | 24 R | | |
| Bromocriptine | 5.3 R | 128 | |
| Bromocriptine | 14 H | | |
| Dopamine | 7.5 T | 18.6 | |
| Dopamine | 2.8 R | | |
| Dopamine | 474 R | | |
| Dopamine + G | 1705 R | 49 | |
| Ergocriptine-S | 0.4 T | 55 | |
| Fencidopam | 2.8 T | 420 | |
| N-0437 | 0.7 T | 93 | |
| (−)Noradrenaline | ~6,000 T | ~6,000 | |
| NPA | 0.4 T | 5.5 | |
| PHNO(+) | 1.2 T | 42 | |
| Quinpirole(±) | 576 R | | |
| Quinpirole(−) | 4.8 T | 17 | |
| Serotonin | ~10,000 T | ~8,000 | |
| SKF-38393 | 157 T | 1600 | |
| SKF-38393 | 9560 R | | |

What we claim is:

1. A homogeneous composition of a 41 kilodalton human dopamine receptor D$_4$ or derivative thereof, having an amino acid sequence that is the sequence identified as Seq. I.D. No. 17.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 388 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: 5'UTR
        ( B ) LOCATION: 1..103

( i x ) FEATURE:
        ( A ) NAME/KEY: exon
        ( B ) LOCATION: 104..388

( i x ) FEATURE:
        ( A ) NAME/KEY: CDS
        ( B ) LOCATION: 104..388

( x i ) SEQUENCE DESCRIPTION: SEQ ID NO:1:

```
CGGGGGCGGG ACCAGGGTCC GGCCGGGGCG TGCCCCCGGG GAGGGACTCC CCGGCTTGCC      60

CCCCGGCGTT GTCCGCGGTG CTCAGCGCCC GCCCGGGCGC GCC ATG GGG AAC CGC      115
                                                Met Gly Asn Arg
                                                 1

AGC ACC GCG GAC GCG GAC GGG CTG CTG GCT GGG CGC GGG CCG GCC GCG      163
Ser Thr Ala Asp Ala Asp Gly Leu Leu Ala Gly Arg Gly Pro Ala Ala
  5              10                  15                  20

GGG GCA TCT GCG GGG GCA TCT GCG GGG CTG GCT GGG CAG GGC GCG GCG      211
Gly Ala Ser Ala Gly Ala Ser Ala Gly Leu Ala Gly Gln Gly Ala Ala
             25                  30                  35

GCG CTG GTG GGG GGC GTG CTG CTC ATC GGC GCG GTG CTC GCG GGG AAC      259
Ala Leu Val Gly Gly Val Leu Leu Ile Gly Ala Val Leu Ala Gly Asn
         40                  45                  50

TCG CTC GTG TGC GTG AGC GTG GCC ACC GAG CGC GCC CTG CAG ACG CCC      307
Ser Leu Val Cys Val Ser Val Ala Thr Glu Arg Ala Leu Gln Thr Pro
     55                  60                  65

ACC AAC TCC TTC ATC GTG AGC CTG GCG GCC GCC GAC CTC CTC CTC GCT      355
Thr Asn Ser Phe Ile Val Ser Leu Ala Ala Ala Asp Leu Leu Leu Ala
 70                  75                  80

CTC CTG GTG CTG CCG CTC TTC GTC TAC TCC GAG                          388
Leu Leu Val Leu Pro Leu Phe Val Tyr Ser Glu
 85                  90                  95
```

( 2 ) INFORMATION FOR SEQ ID NO:2:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Asn Arg Ser Thr Ala Asp Ala Asp Gly Leu Leu Ala Gly Arg
 1               5                  10                  15

Gly Arg Ala Ala Gly Ala Ser Ala Gly Ala Ser Ala Gly Leu Ala Gly
             20                  25                  30
```

| | | | | | | | | | | | | | |
|---|---|---|---|---|---|---|---|---|---|---|---|---|---|
| Gln | Gly | Ala | Ala | Ala | Leu | Val | Gly | Gly | Val | Leu | Leu | Ile | Gly | Ala | Val |
| | | 35 | | | | | 40 | | | | | 45 | | | |
| Leu | Ala | Gly | Asn | Ser | Leu | Val | Cys | Val | Ser | Val | Ala | Thr | Glu | Arg | Ala |
| | 50 | | | | | 55 | | | | | 60 | | | | |
| Leu | Gln | Thr | Pro | Thr | Asn | Ser | Phe | Ile | Val | Ser | Leu | Ala | Ala | Ala | Asp |
| 65 | | | | | 70 | | | | | 75 | | | | | 80 |
| Leu | Leu | Leu | Ala | Leu | Leu | Val | Leu | Pro | Leu | Phe | Val | Tyr | Ser | Glu | |
| | | | | 85 | | | | | 90 | | | | | 95 | |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..20
        ( C ) IDENTIFICATION METHOD: experimental
        ( D ) OTHER INFORMATION: /partial
            / cons_splice= (5'site: YES, 3'site: NO)
            / evidence= EXPERIMENTAL
            / label= IntronI
            / note= "This is the 5' sequence of an intron
            estimated to be 2.0 kilobases in length"

( x i ) SEQUENCE DESCRIPTION: SEQ ID NO:3:

GTGAGCCGCG TCCGGCCGCA                                                                                       20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..20
        ( C ) IDENTIFICATION METHOD: experimental
        ( D ) OTHER INFORMATION: /partial
            / cons_splice= (5'site: NO, 3'site: YES)
            / evidence= EXPERIMENTAL
            / label= IntronI
            / note= "This is the 3' sequence of a intron
            estimated to be 2.0 kilobases in length."

( x i ) SEQUENCE DESCRIPTION: SEQ ID NO:4:

CCTGTGGTGT CGCCGCGCAG                                                                                       20

( 2 ) INFORMATION FOR SEQ ID NO:5:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 1..113

( i x ) FEATURE:

( A ) NAME/KEY: CDS
( B ) LOCATION: 1..113

( x i ) SEQUENCE DESCRIPTION: SEQ ID NO:5:

| GTC | CAG | GGT | GGC | GCG | TGG | CTG | CTG | AGC | CCC | CGC | CTG | TGC | GAC | GCC | CTC | 48 |
| Val | Gln | Gly | Gly | Ala | Trp | Leu | Leu | Ser | Pro | Arg | Leu | Cys | Asp | Ala | Leu | |
| 1 | | | | 5 | | | | | 10 | | | | | 15 | | |

| ATG | GCC | ATG | GAC | GTC | ATG | CTG | TGC | ACC | GCC | TCC | ATC | TTC | AAC | CTG | TGC | 96 |
| Met | Ala | Met | Asp | Val | Met | Leu | Cys | Thr | Ala | Ser | Ile | Phe | Asn | Leu | Cys | |
| | | | 20 | | | | | 25 | | | | | 30 | | | |

| GCC | ATC | AGC | GTG | GAC | AG | | | | | | | | | | | 113 |
| Ala | Ile | Ser | Val | Asp | | | | | | | | | | | | |
| | | 35 | | | | | | | | | | | | | | |

( 2 ) INFORMATION FOR SEQ ID NO:6:

( i ) SEQUENCE CHARACTERISTICS:
( A ) LENGTH: 37 amino acids
( B ) TYPE: amino acid
( D ) TOPOLOGY: linear ( i i ) MOLECULE TYPE: protein ( x i ) SEQUENCE DESCRIPTION: SEQ ID NO:6:

| Val | Gln | Gly | Gly | Ala | Trp | Leu | Leu | Ser | Pro | Arg | Leu | Cys | Asp | Ala | Leu |
| 1 | | | | 5 | | | | | 10 | | | | | 15 | |

| Met | Ala | Met | Asp | Val | Met | Leu | Cys | Thr | Ala | Ser | Ile | Phe | Asn | Leu | Cys |
| | | | 20 | | | | | 25 | | | | | 30 | | |

| Ala | Ile | Ser | Val | Asp |
| | | 35 | | |

( 2 ) INFORMATION FOR SEQ ID NO:7:

( i ) SEQUENCE CHARACTERISTICS:
( A ) LENGTH: 102 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: intron
( B ) LOCATION: 1..102
( C ) IDENTIFICATION METHOD: experimental
( D ) OTHER INFORMATION: /evidence= EXPERIMENTAL
/ label= IntronII ( x i ) SEQUENCE DESCRIPTION: SEQ ID NO:7:

GTGCGCCGCC CTCCCCGCCC GCGCCCCGGC GCCCCCGCGC CCCGCCCGCC GCCCTCACCG    60

CGGCCTGTGC GCTGTCCGGC GCCCCCTCGG CGCTCCCCGC AG    102

( 2 ) INFORMATION FOR SEQ ID NO:8:

( i ) SEQUENCE CHARACTERISTICS:
( A ) LENGTH: 409 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: exon
( B ) LOCATION: 1..409

( i x ) FEATURE:
( A ) NAME/KEY: CDS
( B ) LOCATION: 2..409

( x i ) SEQUENCE DESCRIPTION: SEQ ID NO:8:

```
G   TTC  GTG  GCC  GTG  GCC  GTG  CCG  CTG  CGC  TAC  AAC  CGG  CAG  GGT  GGG        46
    Phe  Val  Ala  Val  Ala  Val  Pro  Leu  Arg  Tyr  Asn  Arg  Gln  Gly  Gly
    1              5                        10                       15

AGC  CGC  CGG  CAG  CTG  CTG  CTC  ATC  GGC  GCC  ACG  TGG  CTG  CTG  TCC  GCG        94
Ser  Arg  Arg  Gln  Leu  Leu  Leu  Ile  Gly  Ala  Thr  Trp  Leu  Leu  Ser  Ala
                    20                       25                       30

GCG  GTG  GCG  GCG  CCC  GTA  CTG  TGC  GGC  CTC  AAC  GAC  GTG  CGC  GGC  CGC       142
Ala  Val  Ala  Ala  Pro  Val  Leu  Cys  Gly  Leu  Asn  Asp  Val  Arg  Gly  Arg
               35                       40                       45

GAC  CCC  GCC  GTG  TGC  CGC  CTG  GAG  GAC  CGC  GAC  TAC  GTG  GTC  TAC  TCG       190
Asp  Pro  Ala  Val  Cys  Arg  Leu  Glu  Asp  Arg  Asp  Tyr  Val  Val  Tyr  Ser
          50                       55                       60

TCC  GTG  TGC  TCC  TTC  TTC  CTA  CCC  TGC  CCG  CTC  ATG  CTG  CTG  CTG  TAC       238
Ser  Val  Cys  Ser  Phe  Phe  Leu  Pro  Cys  Pro  Leu  Met  Leu  Leu  Leu  Tyr
     65                       70                       75

TGG  GCC  ACG  TTC  CGC  GGC  CTG  CAG  CGC  TGG  GAG  GTG  GCA  CGT  CGC  GCC       286
Trp  Ala  Thr  Phe  Arg  Gly  Leu  Gln  Arg  Trp  Glu  Val  Ala  Arg  Arg  Ala
80                       85                       90                       95

AAG  CTG  CAC  GGC  CGC  GCG  CCC  CGC  CGA  CCC  AGC  GGC  CCT  GGC  CCG  CCT       334
Lys  Leu  His  Gly  Arg  Ala  Pro  Arg  Arg  Pro  Ser  Gly  Pro  Gly  Pro  Pro
                    100                      105                      110

TCC  CCC  ACG  CCA  CCC  GCG  CCC  CGC  CTC  CCC  CAG  GAC  CCC  TGC  GGC  CCC       382
Ser  Pro  Thr  Pro  Pro  Ala  Pro  Arg  Leu  Pro  Gln  Asp  Pro  Cys  Gly  Pro
               115                      120                      125

GAC  TGT  GCG  CCC  CCC  GCG  CCC  GGC  CTC                                           409
Asp  Cys  Ala  Pro  Pro  Ala  Pro  Gly  Leu
          130                      135
```

( 2 ) INFORMATION FOR SEQ ID NO:9:

( i ) SEQUENCE CHARACTERISTICS:
        ( A ) LENGTH: 136 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Phe  Val  Ala  Val  Ala  Val  Pro  Leu  Arg  Tyr  Asn  Arg  Gln  Gly  Gly  Ser
1              5                        10                       15

Arg  Arg  Gln  Leu  Leu  Leu  Ile  Gly  Ala  Thr  Trp  Leu  Leu  Ser  Ala  Ala
                    20                       25                       30

Val  Ala  Ala  Pro  Val  Leu  Cys  Gly  Leu  Asn  Asp  Val  Arg  Gly  Arg  Asp
               35                       40                       45

Pro  Ala  Val  Cys  Arg  Leu  Glu  Asp  Arg  Asp  Tyr  Val  Val  Tyr  Ser  Ser
          50                       55                       60

Val  Cys  Ser  Phe  Phe  Leu  Pro  Cys  Pro  Leu  Met  Leu  Leu  Leu  Tyr  Trp
65                       70                       75                       80

Ala  Thr  Phe  Arg  Gly  Leu  Gln  Arg  Trp  Glu  Val  Ala  Arg  Arg  Ala  Lys
                    85                       90                       95

Leu  His  Gly  Arg  Ala  Pro  Arg  Arg  Pro  Ser  Gly  Pro  Gly  Pro  Pro  Ser
               100                      105                      110

Pro  Thr  Pro  Pro  Ala  Pro  Arg  Leu  Pro  Gln  Asp  Pro  Cys  Gly  Pro  Asp
          115                      120                      125

Cys  Ala  Pro  Pro  Ala  Pro  Gly  Leu
          130                      135
```

( 2 ) INFORMATION FOR SEQ ID NO:10:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:10:

TCCCCGGGGT CCCTGCGGCC                                        20

( 2 ) INFORMATION FOR SEQ ID NO:11:

( i ) SEQUENCE CHARACTERISTICS:
      ( A ) LENGTH: 73 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:11:

CCTGTGCGCC CCCCGCGCCC GGCCTCCCCC AGGACCCCTG CGGCCCCGAC TGTGCGCCCC    60

CCGCGCCCGG CCT                                                       73

( 2 ) INFORMATION FOR SEQ ID NO:12:

( i ) SEQUENCE CHARACTERISTICS:
      ( A ) LENGTH: 155 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: exon
      ( B ) LOCATION: 1..155

( i x ) FEATURE:
      ( A ) NAME/KEY: CDS
      ( B ) LOCATION: 2..154

( x i ) SEQUENCE DESCRIPTION: SEQ ID NO:12:

C CCC CCG GAC CCC TGC GGC TCC AAC TGT GCT CCC CCC GAC GCC GTC AGA    49
  Pro Pro Asp Pro Cys Gly Ser Asn Cys Ala Pro Pro Asp Ala Val Arg
  1               5                   10                  15

GCC GCC GCG CTC CCA CCC CAG ACT CCA CCG CAG ACC CGC AGG AGG CGG      97
Ala Ala Ala Leu Pro Pro Gln Thr Pro Pro Gln Thr Arg Arg Arg Arg
                20              25                  30

CGT GCC AAG ATC ACC GGC CGG GAG CGC AAG GCC ATG AGG GTC CTG CCG     145
Arg Ala Lys Ile Thr Gly Arg Glu Arg Lys Ala Met Arg Val Leu Pro
            35              40              45

GTG GTG GTC G                                                       155
Val Val Val
        50

( 2 ) INFORMATION FOR SEQ ID NO:13:

( i ) SEQUENCE CHARACTERISTICS:
      ( A ) LENGTH: 51 amino acids
      ( B ) TYPE: amino acid
      ( D ) TOPOLOGY: linear ( i i ) MOLECULE TYPE: protein ( x i ) SEQUENCE DESCRIPTION: SEQ ID NO:13:

Pro Pro Asp Pro Cys Gly Ser Asn Cys Ala Pro Pro Asp Ala Val Arg

```
         1                 5                          10                          15
Ala   Ala   Ala   Leu   Pro   Pro   Gln   Thr   Pro   Pro   Gln   Thr   Arg   Arg   Arg   Arg
                        20                          25                          30

Arg   Ala   Lys   Ile   Thr   Gly   Arg   Glu   Arg   Lys   Ala   Met   Arg   Val   Leu   Pro
                  35                          40                          45

Val   Val   Val
            50
```

( 2 ) INFORMATION FOR SEQ ID NO:14:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..94

( x i ) SEQUENCE DESCRIPTION: SEQ ID NO:14:

```
GTGGGTTCCT   GTCCTGAGGG   GCGGGGAGGA   GAGGAGGGGG   GGAGTACGAG   GCCGGCTGGG        60

CGGGGGGCGC   TAACGCGGCT   CTCGGCGCCC   CCAG                                        94
```

( 2 ) INFORMATION FOR SEQ ID NO:15:

( i ) SEQUENCE CHARACTERISTICS:
        ( A ) LENGTH: 328 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 1..328

( i x ) FEATURE:
        ( A ) NAME/KEY: CDS
        ( B ) LOCATION: 3..203

( i x ) FEATURE:
        ( A ) NAME/KEY: 3'UTR
        ( B ) LOCATION: 204..328

( i x ) FEATURE:
        ( A ) NAME/KEY: polyA_site
        ( B ) LOCATION: 304

( x i ) SEQUENCE DESCRIPTION: SEQ ID NO:15:

```
GG  GCC  TTC  CTG  CTG  TGC  TGG  ACG  CCC  TTC  TTC  GTG  GTG  CAC  ATC  ACG           47
    Ala  Phe  Leu  Leu  Cys  Trp  Thr  Pro  Phe  Phe  Val  Val  His  Ile  Thr
     1             5                       10                         15

CAG  GCG  CTG  TGT  CCT  GCC  TGC  TCC  GTG  CCC  CCG  CGG  CTG  GTC  AGC  GCC           95
Gln  Ala  Leu  Cys  Pro  Ala  Cys  Ser  Val  Pro  Pro  Arg  Leu  Val  Ser  Ala
               20                        25                        30

GTC  ACC  TGG  CTG  GGC  TAC  GTC  AAC  AGC  GCC  CTC  ACC  CCC  GTC  ATC  TAC          143
Val  Thr  Trp  Leu  Gly  Tyr  Val  Asn  Ser  Ala  Leu  Thr  Pro  Val  Ile  Tyr
          35                        40                        45

ACT  GTC  TTC  AAC  GCC  GAG  TTC  CGC  AAC  GTC  TTC  CGC  AAG  GCC  CTG  CGT          191
Thr  Val  Phe  Asn  Ala  Glu  Phe  Arg  Asn  Val  Phe  Arg  Lys  Ala  Leu  Arg
     50                        55                        60

GCC  TGC  TGC  TGAGCCGGGC  ACCCCCGGAC  GCCCCCGGC  CTGATGGCCA                            240
Ala  Cys  Cys
      65
```

```
GGCCTCAGGG ACCAAGGAGA TGGGGAGGGC GCTTTTGTAC GTTAATTAAA CAAATTCCTT          300

CCCAAACTCA GCTGTGAAGG CTCCTGGG                                             328
```

( 2 ) INFORMATION FOR SEQ ID NO:16:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ala  Phe  Leu  Leu  Cys  Trp  Thr  Pro  Phe  Phe  Val  Val  His  Ile  Thr  Gln
 1              5                        10                       15

Ala  Leu  Cys  Pro  Ala  Cys  Ser  Val  Pro  Pro  Arg  Leu  Val  Ser  Ala  Val
              20                       25                       30

Thr  Trp  Leu  Gly  Tyr  Val  Asn  Ser  Ala  Leu  Thr  Pro  Val  Ile  Tyr  Thr
         35                       40                       45

Val  Phe  Asn  Ala  Glu  Phe  Arg  Asn  Val  Phe  Arg  Lys  Ala  Leu  Arg  Ala
    50                       55                       60

Cys  Cys
65
```

( 2 ) INFORMATION FOR SEQ ID NO:17:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:17:

```
Met  Gly  Asn  Arg  Ser  Thr  Ala  Asp  Ala  Asp  Gly  Leu  Leu  Ala  Gly  Arg
 1              5                        10                       15

Gly  Pro  Ala  Ala  Gly  Ala  Ser  Ala  Gly  Ala  Ser  Ala  Gly  Leu  Ala  Gly
              20                       25                       30

Gln  Gly  Ala  Ala  Ala  Leu  Val  Gly  Gly  Val  Leu  Leu  Ile  Gly  Ala  Val
         35                       40                       45

Leu  Ala  Gly  Asn  Ser  Leu  Val  Cys  Val  Ser  Val  Ala  Thr  Glu  Arg  Ala
    50                       55                       60

Leu  Gln  Thr  Pro  Thr  Asn  Ser  Phe  Ile  Val  Ser  Leu  Ala  Ala  Ala  Asp
65                       70                       75                       80

Leu  Leu  Leu  Ala  Leu  Leu  Val  Leu  Pro  Leu  Phe  Val  Tyr  Ser  Glu  Val
              85                       90                       95

Gln  Gly  Gly  Ala  Trp  Leu  Leu  Ser  Pro  Arg  Leu  Cys  Asp  Ala  Leu  Met
              100                      105                      110

Ala  Met  Asp  Val  Met  Leu  Cys  Thr  Ala  Ser  Ile  Phe  Asn  Leu  Cys  Ala
              115                      120                      125

Ile  Ser  Val  Asp  Arg  Phe  Val  Ala  Val  Ala  Val  Pro  Leu  Arg  Tyr  Asn
    130                      135                      140

Arg  Gln  Gly  Gly  Ser  Arg  Arg  Gln  Leu  Leu  Leu  Ile  Gly  Ala  Thr  Trp
145                      150                      155                      160

Leu  Leu  Ser  Ala  Ala  Val  Ala  Ala  Pro  Val  Leu  Cys  Gly  Leu  Asn  Asp
              165                      170                      175

Val  Arg  Gly  Arg  Asp  Pro  Ala  Val  Cys  Arg  Leu  Glu  Asp  Arg  Asp  Tyr
```

-continued

```
                                180                           185                           190
        Val    Val    Tyr    Ser    Ser    Val    Cys    Ser    Phe    Phe    Leu    Pro    Cys    Pro    Leu    Met
                      195                          200                          205
        Leu    Leu    Leu    Tyr    Trp    Ala    Thr    Phe    Arg    Gly    Leu    Gln    Arg    Trp    Glu    Val
               210                          215                          220
        Ala    Arg    Arg    Ala    Lys    Leu    His    Gly    Arg    Ala    Pro    Arg    Arg    Pro    Ser    Gly
        225                          230                          235                                        240
        Pro    Gly    Pro    Pro    Ser    Pro    Thr    Pro    Pro    Ala    Pro    Arg    Leu    Pro    Gln    Asp
                             245                          250                          255
        Pro    Cys    Gly    Pro    Asp    Cys    Ala    Pro    Pro    Ala    Pro    Gly    Leu    Pro    Pro    Asp
                      260                          265                          270
        Pro    Cys    Gly    Ser    Asn    Cys    Ala    Pro    Pro    Asp    Ala    Val    Arg    Ala    Ala    Ala
                      275                          280                          285
        Leu    Pro    Pro    Gln    Thr    Pro    Pro    Gln    Thr    Arg    Arg    Arg    Arg    Ala    Lys
               290                          295                          300
        Ile    Thr    Gly    Arg    Glu    Arg    Lys    Ala    Met    Arg    Val    Leu    Pro    Val    Val    Val
        305                          310                          315                                        320
        Gly    Ala    Phe    Leu    Leu    Cys    Trp    Thr    Pro    Phe    Phe    Val    Val    His    Ile    Thr
                             325                          330                          335
        Gln    Ala    Leu    Cys    Pro    Ala    Cys    Ser    Val    Pro    Pro    Arg    Leu    Val    Ser    Ala
                      340                          345                          350
        Val    Thr    Trp    Leu    Gly    Tyr    Val    Asn    Ser    Ala    Leu    Asn    Arg    Val    Ile    Tyr
                      355                          360                          365
        Thr    Val    Phe    Asn    Ala    Glu    Phe    Arg    Asn    Val    Phe    Arg    Lys    Ala    Leu    Arg
               370                          375                          380
        Ala    Cys    Cys
        385
```

( 2 ) INFORMATION FOR SEQ ID NO:18:

( i ) SEQUENCE CHARACTERISTICS:
      ( A ) LENGTH: 443 amino acids
      ( B ) TYPE: amino acid
      ( D ) TOPOLOGY: linear ( i i ) MOLECULE TYPE: protein ( i i i ) HYPOTHETICAL: NO ( x i ) SEQUENCE DESCRIPTION: SEQ ID NO:18:

```
        Met    Asp    Pro    Leu    Asn    Leu    Ser    Trp    Tyr    Asp    Asp    Leu    Glu    Arg    Gln
        1                    5                           10                           15
        Asn    Trp    Ser    Arg    Pro    Phe    Asn    Gly    Ser    Asp    Gly    Lys    Ala    Asp    Arg    Pro
                      20                           25                           30
        His    Tyr    His    Tyr    Tyr    Ala    Thr    Leu    Leu    Thr    Leu    Leu    Ile    Ala    Val    Ile
                      35                           40                           45
        Val    Phe    Gly    Asn    Val    Leu    Val    Cys    Met    Ala    Val    Ser    Arg    Glu    Lys    Ala
               50                           55                           60
        Leu    Gln    Thr    Thr    Thr    Asn    Tyr    Leu    Ile    Val    Ser    Leu    Ala    Val    Ala    Asp
        65                           70                           75                                        80
        Leu    Leu    Val    Ala    Thr    Leu    Val    Met    Pro    Trp    Val    Val    Tyr    Leu    Glu    Val
                             85                           90                           95
        Val    Gly    Glu    Trp    Lys    Phe    Ser    Arg    Ile    His    Cys    Asp    Ile    Phe    Val    Thr
                      100                          105                          110
        Leu    Asp    Val    Met    Met    Cys    Thr    Ala    Ser    Ile    Leu    Asn    Leu    Cys    Ala    Ile
                      115                          120                          125
        Ser    Ile    Asp    Arg    Tyr    Thr    Ala    Val    Ala    Met    Pro    Met    Leu    Tyr    Asn    Thr
```

|   |   |   |   |   | 130 |   |   |   |   | 135 |   |   |   |   | 140 |   |   |   |   |
|---|---|---|---|---|---|---|---|---|---|---|---|---|---|---|---|---|---|---|---|

Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Arg Arg Arg Lys Arg Val Asn
    210                 215                 220

Thr Lys Arg Ser Ser Arg Ala Phe Arg Ala His Leu Arg Ala Pro Leu
225             230                 235                 240

Lys Gly Asn Cys Thr His Pro Glu Asp Met Lys Leu Cys Thr Val Ile
                245                 250                 255

Met Lys Ser Asn Gly Ser Phe Pro Val Asn Arg Arg Arg Val Asp Ala
            260                 265                 270

Ala Arg Arg Ala Gln Glu Leu Glu Met Glu Met Leu Ser Ser Thr Ser
        275                 280                 285

Pro Pro Glu Arg Thr Arg Tyr Ser Pro Ile Pro Pro Ser His His Gln
    290                 295                 300

Leu Thr Leu Pro Asp Pro Ser His His Gly Leu His Ser Thr Pro Asp
305                 310                 315                 320

Ser Pro Ala Lys Pro Glu Lys Asn Gly His Ala Lys Asp His Pro Lys
                325                 330                 335

Ile Ala Lys Ile Phe Glu Ile Gln Thr Met Pro Asn Gly Lys Thr Arg
            340                 345                 350

Thr Ser Leu Lys Thr Met Ser Arg Arg Lys Leu Ser Gln Gln Lys Glu
        355                 360                 365

Lys Lys Ala Thr Gln Met Leu Ala Ile Val Leu Gly Val Phe Ile Ile
    370                 375                 380

Cys Trp Leu Pro Phe Phe Ile Thr His Ile Leu Asn Ile His Cys Asp
385                 390                 395                 400

Cys Asn Ile Pro Pro Val Leu Tyr Ser Ala Phe Thr Trp Leu Gly Tyr
                405                 410                 415

Val Asn Ser Ala Val Asn Pro Ile Ile Tyr Thr Thr Phe Asn Ile Glu
            420                 425                 430

Phe Arg Lys Ala Phe Leu Lys Ile Leu His Cys
        435                 440

( 2 ) INFORMATION FOR SEQ ID NO:19:

( i ) SEQUENCE CHARACTERISTICS:
        ( A ) LENGTH: 444 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:19:

Met Asp Pro Leu Asn Leu Ser Trp Tyr Asp Asp Leu Glu Arg Gln
1               5                   10                  15

Asn Trp Ser Arg Pro Phe Asn Gly Ser Glu Gly Lys Ala Asp Arg Pro
            20                  25                  30

His Tyr Asn Tyr Tyr Ala Met Leu Leu Thr Leu Leu Ile Phe Ile Ile

|     |     |     |     | 35  |     |     |     |     | 40  |     |     |     |     | 45  |     |     |     |     |     |
|-----|-----|-----|-----|-----|-----|-----|-----|-----|-----|-----|-----|-----|-----|-----|-----|-----|-----|-----|-----|

Val Phe Gly Asn Val Leu Val Cys Met Ala Val Ser Arg Glu Lys Ala
          50                      55                      60

Leu Gln Thr Thr Thr Asn Tyr Leu Ile Val Ser Leu Ala Val Ala Asp
65                          70                  75                      80

Leu Leu Val Ala Thr Leu Val Met Pro Trp Val Val Tyr Leu Glu Val
                    85                      90                      95

Val Gly Glu Trp Lys Phe Ser Arg Ile His Cys Asp Ile Phe Val Thr
                100                     105                     110

Leu Asp Val Met Met Cys Thr Ala Ser Ile Leu Asn Leu Cys Ala Ile
            115                     120                     125

Ser Ile Asp Arg Tyr Thr Ala Val Ala Met Pro Met Leu Tyr Asn Thr
        130                     135                     140

Arg Tyr Ser Ser Lys Arg Arg Val Thr Val Met Ile Ala Ile Val Trp
145                     150                     155                     160

Val Leu Ser Phe Thr Ile Ser Cys Pro Leu Leu Phe Gly Ile Asn Asn
                    165                     170                     175

Thr Asp Gln Asn Glu Cys Ile Ile Ala Asn Pro Ala Phe Val Val Tyr
                180                     185                     190

Ser Ser Ile Val Ser Phe Tyr Val Pro Phe Ile Val Thr Leu Leu Val
            195                     200                     205

Tyr Ile Lys Ile Tyr Ile Val Leu Arg Lys Arg Arg Lys Arg Val Asn
    210                     215                     220

Thr Lys Arg Ser Ser Arg Ala Phe Arg Ala Asn Leu Lys Thr Pro Leu
225                     230                     235                     240

Lys Gly Asn Cys Thr His Pro Glu Asp Met Lys Leu Cys Thr Val Ile
                245                     250                     255

Met Lys Ser Asn Gly Ser Phe Pro Val Asn Arg Arg Arg Met Asp Ala
                260                     265                     270

Ala Arg Arg Ala Gln Glu Leu Glu Met Glu Met Leu Ser Ser Thr Ser
            275                     280                     285

Pro Pro Glu Arg Thr Arg Tyr Ser Pro Ile Pro Pro Ser His His Gln
    290                     295                     300

Leu Thr Leu Pro Asp Pro Ser His His Gly Leu His Ser Asn Pro Asp
305                     310                     315                     320

Ser Pro Ala Lys Pro Glu Lys Asn Gly His Ala Lys Ile Val Asn Pro
                325                     330                     335

Arg Ile Ala Lys Phe Phe Glu Ile Gln Thr Met Pro Asn Gly Lys Thr
                340                     345                     350

Arg Thr Ser Leu Lys Thr Met Ser Arg Arg Lys Leu Ser Gln Gln Lys
            355                     360                     365

Glu Lys Lys Ala Thr Gln Met Leu Ala Ile Val Leu Gly Val Phe Ile
    370                     375                     380

Ile Cys Trp Leu Pro Phe Phe Ile Thr His Ile Leu Asn Ile His Cys
385                     390                     395                     400

Asp Cys Asn Ile Pro Pro Val Leu Tyr Ser Ala Phe Thr Trp Leu Gly
                405                     410                     415

Tyr Val Asn Ser Ala Val Asn Pro Ile Ile Tyr Thr Thr Phe Asn Ile
                420                     425                     430

Glu Phe Arg Lys Ala Phe Met Lys Ile Leu His Cys
            435                     440

( 2 ) INFORMATION FOR SEQ ID NO:20:

( i ) SEQUENCE CHARACTERISTICS:
    ( A ) LENGTH: 444 amino acids
    ( B ) TYPE: amino acid
    ( D ) TOPOLOGY: linear ( i i ) MOLECULE TYPE: protein ( i i i ) HYPOTHETICAL: NO ( x i ) SEQUENCE DESCRIPTION: SEQ ID NO:20:

```
Met Ala Pro Leu Ser Gln Ile Ser Thr His Leu Asn Ser Thr Cys Gly
  1               5                  10                  15
Ala Glu Asn Ser Thr Gly Val Asn Arg Ala Arg Pro His Ala Tyr Tyr
                 20                  25                  30
Ala Leu Ser Tyr Cys Ala Leu Ile Leu Ala Ile Ile Phe Gly Asn Gly
             35                  40                  45
Leu Val Cys Ala Ala Val Ile Arg Glu Arg Ala Leu Gln Thr Thr Thr
         50                  55                  60
Asn Tyr Leu Val Val Ser Leu Ala Val Ala Asp Leu Leu Val Ala Thr
 65                  70                  75                  80
Leu Val Met Pro Trp Val Val Tyr Leu Glu Val Thr Gly Gly Val Trp
                 85                  90                  95
Asn Phe Ser Arg Ile Cys Cys Asp Val Phe Val Thr Leu Asp Val Met
            100                 105                 110
Met Cys Thr Ala Ser Ile Leu Asn Leu Cys Ala Ile Ser Ile Asp Arg
        115                 120                 125
Tyr Thr Ala Val Val Met Pro Val His Tyr Gln His Gly Thr Gly Gln
    130                 135                 140
Ser Ser Cys Arg Arg Val Ala Leu Met Ile Thr Ala Val Trp Val Leu
145                 150                 155                 160
Ala Phe Ala Val Ser Cys Pro Leu Leu Phe Gly Phe Asn Thr Thr Gly
                165                 170                 175
Asp Pro Ser Ile Cys Ser Ile Ser Asn Pro Asp Phe Val Ile Tyr Ser
            180                 185                 190
Ser Val Val Ser Phe Tyr Val Pro Phe Gly Val Thr Val Leu Val Tyr
        195                 200                 205
Ala Arg Ile Tyr Ile Val Leu Arg Gln Arg Gln Arg Ile Leu Thr Arg
    210                 215                 220
Gln Asn Ser Gln Cys Ile Ser Ile Arg Pro Gly Phe Pro Gln Gln Ser
225                 230                 235                 240
Ser Cys Leu Arg Leu His Pro Ile Arg Gln Phe Ser Ile Arg Ala Arg
                245                 250                 255
Phe Leu Ser Asp Ala Thr Gly Gln Met Glu His Ile Glu Asp Lys Gln
            260                 265                 270
Tyr Pro Gln Lys Cys Gln Asp Pro Leu Leu Ser His Leu Gln Pro Pro
        275                 280                 285
Ser Pro Gly Gln Thr His Gly Gly Leu Lys Arg Tyr Tyr Ser Ile Cys
    290                 295                 300
Gln Asp Thr Ala Leu Arg His Pro Ser Leu Glu Gly Gly Ala Gly Met
305                 310                 315                 320
Ser Pro Val Glu Arg Thr Arg Asn Ser Leu Ser Pro Thr Met Ala Pro
                325                 330                 335
Lys Leu Ser Leu Glu Val Arg Lys Leu Ser Asn Gly Arg Leu Ser Thr
            340                 345                 350
Ser Leu Arg Leu Gly Pro Leu Gln Pro Arg Gly Val Pro Leu Arg Glu
        355                 360                 365
```

```
            Lys  Lys  Ala  Thr  Gln  Met  Val  Val  Ile  Val  Leu  Gly  Ala  Phe  Ile  Val
                 370                 375                           380

Cys  Trp  Leu  Pro  Phe  Phe  Leu  Thr  His  Val  Leu  Asn  Thr  His  Cys  Gln
            385                      390                      395                           400

Ala  Cys  His  Val  Ser  Pro  Glu  Leu  Tyr  Arg  Ala  Thr  Thr  Trp  Leu  Gly
                                405                      410                      415

Tyr  Val  Asn  Ser  Ala  Leu  Asn  Pro  Val  Ile  Tyr  Thr  Thr  Phe  Asn  Val
                                420                 425                      430

Glu  Phe  Arg  Lys  Ala  Phe  Leu  Lys  Ile  Leu  Ser  Cys
                      435                      440
```

( 2 ) INFORMATION FOR SEQ ID NO:21:

( i ) SEQUENCE CHARACTERISTICS:
        ( A ) LENGTH: 446 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:21:

```
            Met  Arg  Thr  Leu  Asn  Thr  Ser  Ala  Met  Asp  Gly  Thr  Gly  Leu  Val  Val
            1                   5                    10                           15

Glu  Arg  Asp  Phe  Ser  Val  Arg  Ile  Leu  Thr  Ala  Cys  Phe  Leu  Ser  Leu
                           20                      25                      30

Leu  Ile  Leu  Ser  Thr  Leu  Leu  Gly  Asn  Thr  Leu  Val  Cys  Ala  Ala  Val
                           35                      40                      45

Ile  Arg  Phe  Arg  His  Leu  Arg  Ser  Lys  Val  Thr  Asn  Phe  Phe  Val  Ile
                      50                      55                      60

Ser  Leu  Ala  Val  Ser  Asp  Leu  Leu  Val  Ala  Val  Leu  Val  Met  Pro  Trp
            65                      70                      75                           80

Lys  Ala  Val  Ala  Glu  Ile  Ala  Gly  Phe  Trp  Pro  Phe  Gly  Ser  Phe  Cys
                                85                      90                      95

Asn  Ile  Trp  Val  Ala  Phe  Asp  Ile  Met  Cys  Ser  Thr  Ala  Ser  Ile  Leu
                                100                     105                     110

Asn  Leu  Cys  Val  Ile  Ser  Val  Asp  Arg  Tyr  Trp  Ala  Ile  Ser  Ser  Pro
                      115                     120                     125

Phe  Arg  Tyr  Glu  Arg  Lys  Met  Thr  Pro  Lys  Ala  Ala  Phe  Ile  Leu  Ile
                      130                     135                     140

Ser  Val  Ala  Trp  Thr  Leu  Ser  Val  Leu  Ile  Ser  Phe  Ile  Pro  Val  Gln
            145                     150                     155                          160

Leu  Ser  Trp  His  Lys  Ala  Lys  Pro  Thr  Ser  Pro  Ser  Asp  Gly  Asn  Ala
                           165                     170                     175

Thr  Ser  Leu  Ala  Glu  Thr  Ile  Asp  Asn  Cys  Asp  Ser  Ser  Leu  Ser  Arg
                           180                     185                     190

Thr  Tyr  Ala  Ile  Ser  Ser  Ser  Val  Ile  Ser  Phe  Tyr  Ile  Pro  Val  Ala
                           195                     200                     205

Ile  Met  Ile  Val  Thr  Tyr  Thr  Arg  Ile  Tyr  Arg  Ile  Ala  Gln  Lys  Gln
                      210                     215                     220

Ile  Arg  Arg  Ile  Ala  Ala  Leu  Glu  Arg  Ala  Ala  Val  His  Ala  Lys  Asn
            225                     230                     235                          240

Cys  Gln  Thr  Thr  Thr  Gly  Asn  Gly  Lys  Pro  Val  Glu  Cys  Ser  Gln  Pro
                           245                     250                     255

Glu  Ser  Ser  Phe  Lys  Met  Ser  Phe  Lys  Arg  Glu  Thr  Lys  Val  Leu  Lys
                           260                     265                     270
```

```
Thr Leu Ser Val Ile Met Gly Val Phe Val Cys Cys Trp Leu Pro Phe
        275             280                 285
Phe Ile Leu Asn Cys Ile Leu Pro Phe Cys Gly Ser Gly Glu Thr Gln
        290             295                 300
Pro Phe Cys Ile Asp Ser Asn Thr Phe Asp Val Phe Val Trp Phe Gly
305             310                 315                     320
Trp Ala Asn Ser Ser Leu Asn Pro Ile Ile Tyr Ala Phe Asn Ala Asp
                325                 330                 335
Phe Arg Lys Ala Phe Ser Thr Leu Leu Gly Cys Tyr Arg Leu Cys Pro
                340             345                 350
Ala Thr Asn Asn Ala Ile Glu Thr Val Ser Ile Asn Asn Asn Gly Ala
        355             360                 365
Ala Met Phe Ser Ser His His Glu Pro Arg Gly Ser Ile Ser Lys Glu
    370             375                 380
Cys Asn Leu Val Tyr Leu Ile Pro His Ala Val Gly Ser Ser Glu Asp
385             390                 395                     400
Leu Lys Lys Glu Glu Ala Ala Gly Ile Ala Arg Pro Leu Glu Lys Leu
                405             410                 415
Ser Pro Ala Leu Ser Val Ile Leu Asp Tyr Asp Thr Asp Val Ser Leu
            420             425                 430
Glu Lys Ile Gln Pro Ile Thr Gln Asn Gly Gln His Pro Thr
        435             440                 445
```

( 2 ) INFORMATION FOR SEQ ID NO:22:

( i ) SEQUENCE CHARACTERISTICS:
( A ) LENGTH: 446 amino acids
( B ) TYPE: amino acid
( D ) TOPOLOGY: linear ( i i ) MOLECULE TYPE: protein ( i i i ) HYPOTHETICAL: NO ( x i ) SEQUENCE DESCRIPTION: SEQ ID NO:22:

```
Met Ala Pro Asn Thr Ser Thr Met Asp Glu Ala Gly Leu Pro Ala Glu
1               5                   10                  15
Arg Asp Phe Ser Phe Arg Ile Leu Thr Ala Cys Phe Leu Ser Leu Leu
                20              25                  30
Ile Leu Ser Thr Leu Leu Gly Asn Thr Leu Val Cys Ala Ala Val Ile
            35              40                  45
Arg Phe Arg His Leu Arg Ser Lys Val Thr Asn Phe Phe Val Ile Ser
        50              55                  60
Leu Ala Val Ser Asp Leu Leu Val Ala Val Leu Val Met Pro Trp Lys
65              70                  75                      80
Ala Val Ala Glu Ile Ala Gly Phe Trp Pro Phe Gly Ser Phe Cys Asn
                85                  90                  95
Ile Trp Val Ala Phe Asp Ile Met Cys Ser Thr Ala Ser Ile Leu Asn
            100                 105                 110
Leu Cys Val Ile Ser Val Asp Arg Tyr Trp Ala Ile Ser Ser Pro Phe
        115                 120                 125
Gln Tyr Glu Arg Lys Met Thr Pro Lys Ala Ala Phe Ile Leu Ile Ser
    130                 135                 140
Val Ala Trp Thr Leu Ser Val Leu Ile Ser Phe Ile Pro Val Gln Leu
145                 150                 155                 160
Ser Trp His Lys Ala Lys Pro Thr Trp Pro Leu Asp Gly Asn Phe Thr
                165                 170                 175
```

| | | | | | | | | | | | | | |
|---|---|---|---|---|---|---|---|---|---|---|---|---|---|
| Ser | Leu | Glu | Asp 180 | Thr | Glu | Asp | Asn 185 | Cys | Asp | Thr | Arg | Leu 190 | Ser | Arg |
| Thr | Tyr | Ala 195 | Ile | Ser | Ser | Ser | Leu 200 | Ile | Ser | Phe | Tyr | Ile 205 | Pro | Val | Ala |
| Ile | Met 210 | Ile | Val | Thr | Tyr | Thr 215 | Ser | Ile | Tyr | Arg | Ile 220 | Ala | Gln | Leu | Gln |
| Ile 225 | Arg | Arg | Ile | Ser | Ala 230 | Leu | Glu | Arg | Ala | Ala 235 | Val | His | Ala | Lys | Asn 240 |
| Cys | Gln | Thr | Thr | Ala 245 | Gly | Asn | Gly | Asn | Pro 250 | Val | Glu | Cys | Ala | Gln 255 | Ser |
| Glu | Ser | Ser | Phe 260 | Lys | Met | Ser | Phe | Lys 265 | Arg | Glu | Thr | Lys | Val 270 | Leu | Lys |
| Thr | Leu | Ser 275 | Val | Ile | Met | Gly | Val 280 | Phe | Val | Cys | Cys | Trp 285 | Leu | Pro | Phe |
| Phe | Ile 290 | Ser | Asn | Cys | Met | Val 295 | Pro | Phe | Cys | Gly | Ser 300 | Glu | Glu | Thr | Gln |
| Pro 305 | Phe | Cys | Ile | Asp | Ser 310 | Ile | Thr | Phe | Asp | Val 315 | Phe | Val | Trp | Phe | Gly 320 |
| Trp | Ala | Asn | Ser | Ser 325 | Leu | Asn | Pro | Ile | Ile 330 | Tyr | Ala | Phe | Asn | Ala 335 | Asp |
| Phe | Gln | Lys | Ala 340 | Phe | Ser | Thr | Leu | Leu 345 | Gly | Cys | Tyr | Arg | Leu 350 | Cys | Pro |
| Thr | Thr | Asn 355 | Asn | Ala | Ile | Glu | Thr 360 | Val | Ser | Ile | Asn | Asn 365 | Asn | Gly | Ala |
| Val | Val 370 | Phe | Ser | Ser | His | His 375 | Glu | Pro | Arg | Gly | Ser 380 | Ile | Ser | Lys | Asp |
| Cys 385 | Asn | Leu | Val | Tyr | Leu 390 | Ile | Pro | His | Ala | Val 395 | Gly | Ser | Ser | Glu | Asp 400 |
| Leu | Lys | Lys | Glu | Glu 405 | Ala | Gly | Gly | Ile | Ala 410 | Lys | Pro | Leu | Glu | Lys 415 | Leu |
| Ser | Pro | Ala | Leu 420 | Ser | Val | Ile | Leu | Asp 425 | Tyr | Asp | Thr | Asp | Val 430 | Ser | Leu |
| Glu | Lys | Ile 435 | Gln | Pro | Val | Thr | His 440 | Ser | Gly | Gln | His | Ser 445 | Thr | | |